(12) United States Patent
Sekaly et al.

(10) Patent No.: US 8,647,822 B2
(45) Date of Patent: Feb. 11, 2014

(54) DETERMINING WHETHER A TEST COMPOUND MODULATES PD-1 ACTIVITY IN ACTIVATED IMMUNE CELLS USING GENE EXPRESSION PROFILES

(75) Inventors: Rafick-Pierre Sekaly, St.-Laurent (CA); Elias Haddad, Saint-Laurent (CA); Bruce Walker, Charlestown, MA (US); Quentin Eichbaum, Charlestown, MA (US)

(73) Assignees: Oregon Health & Science University, Portland, OR (US); Massachusetts General Hospital, Boston, MA (US)

( * ) Notice: Subject to any disclaimer, the term of this patent is extended or adjusted under 35 U.S.C. 154(b) by 807 days.

(21) Appl. No.: 12/745,220

(22) PCT Filed: Nov. 28, 2008

(86) PCT No.: PCT/CA2008/002095
§ 371 (c)(1),
(2), (4) Date: Sep. 27, 2010

(87) PCT Pub. No.: WO2009/067812
PCT Pub. Date: Jun. 4, 2009

(65) Prior Publication Data
US 2011/0008777 A1  Jan. 13, 2011

Related U.S. Application Data

(60) Provisional application No. 60/990,718, filed on Nov. 28, 2007.

(51) Int. Cl.
*C12Q 1/68* (2006.01)
(52) U.S. Cl.
USPC .......................................... 435/6.11; 435/6.13
(58) Field of Classification Search
USPC ................................................ 435/6.11, 6.13
See application file for complete search history.

(56) References Cited

U.S. PATENT DOCUMENTS

| 6,365,352 B1 * | 4/2002 | Yerramilli et al. ........... 435/6.11 |
| 2003/0044768 A1 | 3/2003 | Wood et al. |
| 2004/0033497 A1 * | 2/2004 | Alarcon-Riquelme et al. .. 435/6 |

FOREIGN PATENT DOCUMENTS

WO  WO 2006/121168 A1  11/2006

OTHER PUBLICATIONS

Barber et al., "Restoring function in exhausted CD8 T cells during chronic viral infection," *Nature Publishing Group*, vol. 439, pp. 682-687, 2006.
Chemnitz et al., "RNA fingerprints provide direct evidence for the inhibitory role of TGFβ and PD-1 on CD4+ T cells in Hodgkin lymphoma," *Blood*, vol. 110, No. 9, pp. 3226-3233, 2007.
Goldberg et al., "Role of PD-1 and its ligand, B7-H1, in early fate decisions of CD8 T cells," *Blood*, vol. 110, No. 1, pp. 186-192, 2007.
Hoff et al., "The tyrosine phosphatase SHP-2 regulates differentiation and apoptosis of individual primary T lymphocytes," *European Journal of Immunology*, vol. 37, pp. 1072-1086, 2007.
Lu et al., "Site-Specific Incorporation of a Phosphotyrosine Mimetic Reveals a Role for Tyrosine Phosphorylation of SHP-2 in Cell Signaling," *Molecular Cell*, vol. 8, pp. 759-769, 2001.
Nishimura et al., "Autoimmune Dilated Cardiomyopathy in PD-1 Receptor-Deficient Mice," *Science*, vol. 291, pp. 319-322, 2001.
Nishimura et al., "Development of Lupus-like Autoimmune Diseases by Disruption of the *PD-1* Gene Encoding an ITIM Motif-Carrying Immunoreceptor," *Immunity*, vol. 11, pp. 141-151, 1999.
Özkaynak et al., "Programmed Death-1 Targeting Can Promote Allograft Survival," *The Journal of Immunology*, vol. 169, pp. 6546-6553, 2002.
Parry et al., "CTLA-4 and PD-1 Receptors Inhibit T-Cell Activation by Distinct Mechanisms," *Molecular and Cellular Biology*, vol. 25, No. 21, pp. 9543-9553, 2005.
Riley et al., "The road to recovery: translating PD-1 biology into clinical benefit," *TRENDS in Immunology*, vol. 28, No. 2, pp. 48-50, 2007.
Thompson et al., "PD-1Is Expressed by Tumor-Infiltrating Immune Cells and Is Associated with Poor Outcome for Patients with Renal Cell Carcinoma," *Clinical Cancer Research 2007*, vol. 13, pp. 1757-1761, 2007.
Velu et al., "Elevated Expression Levels of Inhibitory Receptor Programmed Death 1 on Simian Immunodeficiency Virus-Specific CD8 T Cells during Chronic Infection but Not after Vaccination," *Journal of Virology*, vol. 81, No. 11, pp. 5819-5828, 2007.
International Search Report issued in International Application No. PCT/CA2008/002095 on Mar. 5, 2009 (4 pages).
Written Opinion of the International Searching Authority issued in International Application No. PCT/CA2008/002095 on Mar. 5, 2009 (5 pages).
Extended European Search Report, issued in European Patent Application No. EP 08853672.7 on Jul. 19, 2011 (5 pages).

* cited by examiner

*Primary Examiner* — Kenneth Horlick
(74) *Attorney, Agent, or Firm* — Duane Morris LLP; Nicholas A. Zachariades

(57) ABSTRACT

Modulation of PD-1 activity in the presence or absence of an agent as measured by a gene expression profile of at least two genes is provided. Reagents, kits, methods and uses thereof for the modulation of immune function comprise the identification of modulators of PD-1 activity.

6 Claims, 6 Drawing Sheets

DETERMINING WHETHER A TEST COMPOUND MODULATES PD-1 ACTIVITY IN ACTIVATED IMMUNE CELLS USING GENE EXPRESSION PROFILES

CROSS REFERENCE TO RELATED APPLICATIONS

This is the U.S. National Stage of International Application No. PCT/CA2008/002095, filed on Nov. 28, 2008, which was published in English under PCT Article 21(2), which in turn claims the benefit, under 35 U.S.C. §119(e), of U.S. provisional application No. 60/990,718 filed on Nov. 28, 2007, the content of which is incorporated herein by reference in its entirety.

SEQUENCE LISTING

This application contains a Sequence Listing in computer readable form entitled "85366-01_SeqList", created May 27, 2010 having a size of ~4,700 kb. The computer readable form is incorporated herein by reference.

TECHNICAL FIELD

The present invention generally relates to methods, kits and reagents and uses thereof for example in immune response modulation.

BACKGROUND ART

PD-1, a member of the immunoglobulin (Ig) superfamily, is highly upregulated on activated lymphocytes and monocytes. PD-1 was first identified by subtraction hybridization of a T-cell hybridoma undergoing programmed cell death. PD-1 is expressed on activated $CD4^+$ and $CD8^+$ T cells, B cells and myeloid cells. It interacts with its two known ligands PD-L1 (B7-H1) and PD-L2 (B7-DC). PD-L1 is constitutively expressed on splenic T cells, B cells, monocytes, macrophages and dendritic cells (DCs), and its expression can be induced by activation of T lymphocytes, monocytes, macrophages and DCs. PD-L2 is expressed on non-lymphoid tissues and is upregulated on monocytes and DCs after activation.

PD-1 ligation seems to have an inhibitory effect on the immune response to viral infections; hence following infection with adenovirus, $PD-1^{-/-}$ mice exhibited increased proliferation of effector T-cells in the liver and enhanced virus clearance. Similar results were obtained also in a murine model of Herpes simplex virus (HSV) infection where administration of anti-PD-L1 restored HSV-1 specific responses. More recently, Barber et al. confirmed that PD-1 is upregulated on $CD8^+$ T cells from both acute and chronic (lab-derived strains) LCMV infected mice; however, while PD-1 expression was lost on $CD8^+$ T cells upon viral clearance, it remained upregulated on CD8 T cells from chronically-infected mice (Barber et al., 2006, Nature 439(7077): 682-687). Blocking the PD-1/PD-L1 pathway through the administration of PD-1- or PD-L1-specific antibodies into mice chronically infected with LCMV restored cytokine secretion, cytotoxic activity and the capacity of exhausted $CD8^+$ T cells to proliferate and, to decrease viral load.

Also, PD-1-deficient mice exhibit an autoimmune phenotype. PD-1 deficiency in the C57BL/6 mice results in chronic progressive lupus-like glomerulonephritis and arthritis (Nishimura et al., 1999, Immunity 11(2): 141-151). In Balb/c mice, PD-1 deficiency leads to severe cardiomyopathy due to the presence of heart-tissue-specific self-reacting antibodies (Nishimura et al., 2001, Science 291(5502): 319-322).

Given the role of PD-1 activity in immune function, there is a need for the development of reagents, kits and methods for modulation of the PD-1-associated processes.

SUMMARY OF THE INVENTION

The present invention generally relates to methods, kits and reagents and uses thereof for example in immune response modulation. In an embodiment, such immune response modulation is associated with PD-1 expression and/or activity.

In a first aspect, the present invention provides a method of determining whether a test compound modulates PD-1 activity comprising:
    (a) providing an activated immune cell expressing PD-1;
    (b) determining a gene expression profile of said immune cell in the presence of said test compound;
    (c) comparing said gene expression profile to a corresponding reference gene expression profile determined in the absence of said test compound;
wherein said gene expression profile comprises a candidate expression value for at least two genes, wherein said at least two genes are selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, LTB, MYH9, CLIP3, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAM3, BAZ1A, IL3, FOS, HES4, TIMP1, TNS3, NFKBIA, CGA, TSC22D1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, PLAGL2, KLF2, PRR14, BIRC3, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, TMEM187, C6orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5;
and wherein said reference gene expression profile comprises a reference expression value for said at least two genes; and
    (d) determining whether said test compound modulates PD-1 activity based on said comparison.

In another aspect, the present invention provides a method of determining whether a subject suffers from a disease or condition associated with altered PD-1 activity, said method comprising:
    (a) providing a sample comprising activated immune cells from said subject;
    (b) contacting said sample with a ligand for PD-1;
    (c) determining a gene expression profile of said sample;
    (d) comparing said gene expression profile to a corresponding reference gene expression profile;

wherein said gene expression profile comprises a candidate expression value for at least two genes, wherein said at least two genes are selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, LTB, MYH9, CLIP3, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAM3, BAZ1A, IL3, FOS, HES4, TIMP1, TNS3, NFKBIA, CGA, TSC22D1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, PLAGL2, KLF2, PRR14, BIRC3, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, TMEM187, C6orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5;

and wherein said reference gene expression profile comprises a reference expression value for said at least two genes; and (e) determining whether said subject suffers from a disease or condition associated with altered PD-1 activity based on said comparison.

In an embodiment, the above-mentioned reference expression value corresponds to the level of expression of said at least two genes in the absence of an inhibitor or agonist of PD-1 activity and wherein a difference in said gene expression profile relative to said reference gene expression profile is indicative that said test compound modulates PD-1 activity.

In another embodiment, the above-mentioned reference expression value corresponds to the level of expression of said at least two genes in the presence of an inhibitor of PD-1 activity, and wherein a similarity in said gene expression profile relative to said reference gene expression profile is indicative that said test compound inhibits PD-1 activity.

In another embodiment, the above-mentioned reference expression value corresponds to the level of expression of said at least two genes in the presence of an agonist of PD-1 activity, and wherein a similarity in said gene expression profile relative to said reference gene expression profile is indicative that said compound increases PD-1 activity.

In another embodiment, the above-mentioned reference expression value corresponds to the level of expression of said at least two genes in a control sample obtained from a subject known not to suffer from a disease or condition associated with altered PD-1 activity, and wherein a difference in said gene expression profile relative to said reference gene expression profile is indicative that subject suffers from a disease or condition associated with altered PD-1 activity.

In another embodiment, the above-mentioned reference expression value corresponds to the level of expression of said at least two genes in a control sample obtained from a subject suffering from a disease or condition associated with altered PD-1 activity, and wherein a similarity in said gene expression profile relative to said reference gene expression profile is indicative that subject suffers from a disease or condition associated with altered PD-1 activity.

In an embodiment, the above-mentioned expression value is obtained by determining the level of expression of a nucleic acid or polypeptide encoded thereby comprising a sequence selected from SEQ ID NOs: 1-492.

In an embodiment, the above-mentioned gene expression profile is determined after about 30 minutes of activation, and wherein said gene expression profile comprises a candidate expression value for at least two genes selected from FAM65A, E4F1, CBFA2T3, CENPE, SPEN, TNF, BAT2D1, SPTBN1, BRD2, CCAR1, RPL7L1, MIDN, VHL, PCNT, RUNX3, TJAP1, MACF1, MYH9, CLIP3, SNX26, CDK5RAP2, BAZ1A, FOS, EIF4G3, DUSP1, SLC9A1, MEF2D, SNAPC4, SRRM2, KLF2, PRR14, BHLHB2, PPP1R15A, AUTS2, SETD2, CENPF, FOSB, EGR2, PHACTR4, ULK1, GNL3L, ZCCHC6, ITPR3, ZFP36, NOTCH1, POLE and EGR4.

In another embodiment, the above-mentioned gene expression profile is determined after about 3 hours of activation, and wherein said gene expression profile comprises a candidate expression value for at least two genes selected from E4F1, CBFA2T3, MT1A, ANKRD5, KLF6, SPEN, TNF, BAT2D1, ZYX, SPTBN1, SLA, SOCS1, OSGIN1, BRD2, VGF, TNFSF14, RPL28, CSF2, CCAR1, RPL7L1, MIDN, LUZP1, VHL, PCNT, SPRY1, RUNX3, RDH10, DDEF1, GZMB, TJAP1, MACF1, JMJD1C, MYH9, CLIP3, SNX26, TAGAP, FAM50A, CDK5RAP2, TAF1C, KIAA1754, SUPT6H, SH2D2A, ATP6V0A4, TNFRSF8, ITGA5, IL3, TIMP1, SLC9A1, MEF2D, SNAPC4, DPP9, SRRM2, CD69, IRX5, PLAGL2, KLF2, PRR14, FSCN1, LTBP4, USP11, BHLHB2, ARC, PPP1R15A, AUTS2, MARVELD3, SETD2, CENPF, CBX6, ULK1, GNL3L, ZCCHC6, ITPR3, MT2A, NFATC1, ZFP36, BCL9, NOTCH1, POLE, CREBBP, ACVR1, ICOS and MAG1.

In another embodiment, the above-mentioned gene expression profile is determined after about 6 hours of activation, and wherein said gene expression profile comprises a candidate expression value for at least two genes selected from CD55, DIP, STS-1, CD70, BACH2, REL, KIAA0831, CBFA2T3, KLF6, SMOX, FBXO34, LZTS1, LAMP3, SPEN, SH2B3, ATP1B1, SLA, PLAU, SOCS1, BRD2, PTPN6, TNFSF14, CD97, CSF2, CD83, SPRY1, RUNX3, MBP, RDH10, LTB, MYH9, CCDC64, TAGAP, TRAF1, LRRC8C, IL23A, SH2D2A, IL21R, MAPRE2, TMEM158, IL3, FOS, TNS3, NFKBIA, TSC22D1, ATP6V1B2, DUSP1, SLC9A1, GPR171, CD27, TNFRSF21, TBC1D10C, KLF6, LTBP4, MARVELD3, ADORA2A, CCL4L1, PTPN22, PRKCH, BIRC3, C6orf190, ADM, EOMES, POU2AF1, NFATC1, LY96, ACVR1, MYC, CCL1, CXCR3, MAG1 and FXYD5.

In another embodiment, the above-mentioned gene expression profile is determined after about 18 hours of activation, and wherein said gene expression profile comprises a candidate expression value for at least two genes selected from CD55, NFKB2, TPST2, CST7, GNG4, CD70, REL, PAM, KIAA0831, LOC197322, IL2RA, IL13, CBFA2T3, KRT1, MT1A, NQO1, FBXO34, LAMP3, TNFSF14, IL2, CD97, CSF2, CD83, BCL2L1, CCL20, SPRY1, BCL2A1, MBP, RHOU, RDH10, HTR2B, GZMB, RCBTB2, RGS16, LTB, GBE1, CCDC64, PHEX, TAGAP, TRAF1, CDK5RAP2, LRRC8C, IL23A, SH2D2A, IL21R, ATP6V0A4, ITGA5, JAM3, IL3, HES4, TNS3, NFKBIA, CGA, ATP6V1B2, GPR171, CD27, ALDOC, METT11D1, CD69, PLAGL2, KLF2, BIRC3, IGFBP2, RXRA, ARG2, CENPF, ADORA2A, LAIR2, PTPN22, GNL3L, MFSD2, TMEM187, C6orf190, ADM, POU2AF1, C1orf165, PFKFB4, NR4A2, CCL1 and ICOS.

In an embodiment, the above-mentioned immune cell is a T cell. In a further embodiment, the above-mentioned T cell is a CD4+ T cell. In a further embodiment, the above-mentioned CD4+ T cell is a CD4+ T cell line or a primary CD4+ T cell. In an embodiment, the above-mentioned CD4+ T cell line is a Jurkat T cell line.

In an embodiment, the above-mentioned method further comprises activation of a T cell thereby to provide said activated T cell.

In another embodiment, the above-mentioned T cell is activated using a ligand for the T-cell receptor and for a co-stimulatory molecule. In a further embodiment, the above-mentioned T cell is activated using a first antibody, or a fragment thereof, directed against CD3 and a second antibody, or a fragment thereof, directed against CD28.

In an embodiment, the above-mentioned method comprises determining the expression value of at least 5 genes. In another embodiment, the above-mentioned method comprises determining the expression value of at least 10 genes.

In another aspect, the present invention provides a kit comprising a collection of two or more isolated nucleic acids, their complements, or portions thereof, wherein said two or more nucleic acids correspond to nucleotide sequences of two or more genes selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, LTB, MYH9, CLIP3, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAM3, BAZ1A, IL3, FOS, HES4, TIMP1, TNS3, NFKBIA, CGA, TSC22D1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, PLAGL2, KLF2, PRR14, BIRC3, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, TMEM187, C6orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5, together with instructions setting forth the above-mentioned method.

In another aspect, the present invention provides a kit comprising
(a) a collection of two or more oligonucleotides that hybridize under high stringency conditions to one or more nucleotide sequences of at least two genes selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, LTB, MYH9, CLIP3, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAM3, BAZ1A, IL3, FOS, HES4, TIMP1, TNS3, NFKBIA, CGA, TSC22D1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, PLAGL2, KLF2, PRR14, BIRC3, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, TMEM187, C6orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5, or to a complement thereof; or
(b) a collection of two or more antibodies that specifically binds to polypeptides encoded by said at least two genes; together with instructions setting forth the above-mentioned method.

In an embodiment, the above-mentioned nucleic acids comprise a nucleotide sequence selected from the group consisting of the odd-numbered SEQ ID NOs: among SEQ ID NOs: 1-492 (SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489 and 491).

In another embodiment, the above-mentioned two or more oligonucleotides are: (a) two or more oligonucleotides comprising a nucleotide sequence selected from SEQ ID NOs: 493-671; a complement of the two or more oligonucleotides of (a); a fragment of (a) or (b).

In another embodiment, the above-mentioned polypeptides comprise an amino acid sequence selected from the group consisting of the even-numbered SEQ ID NOs: among SEQ ID NOs: 1-492 (SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490 and 492).

In an embodiment, the above-mentioned method is an in vitro method.

Other objects, advantages and features of the present invention will become more apparent upon reading of the following non-restrictive description of specific embodiments thereof, given by way of example only with reference to the accompanying drawings.

DISCLOSURE OF INVENTION

Figure 1:
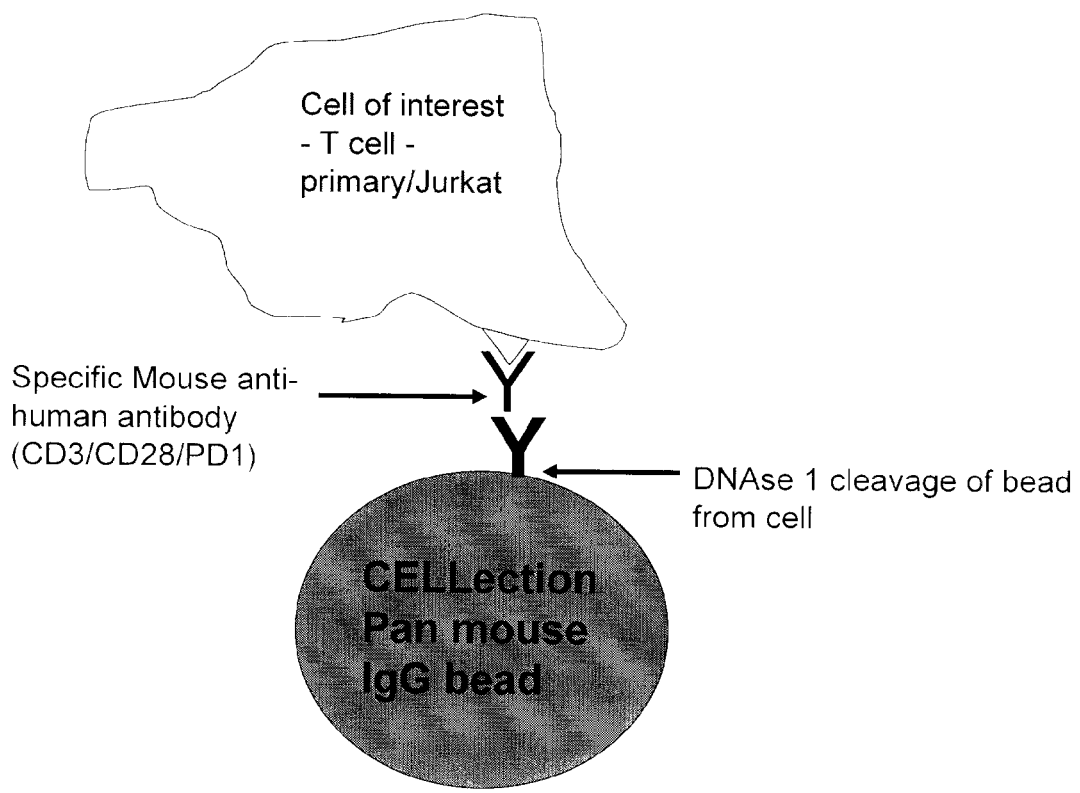
FIG. 1 illustrates the experimental system used to perform the experiments described herein.

In the studies described herein, the gene expression profile/signature of T cells activated in the presence or absence of a ligand to PD-1 was analyzed. It was found that the presence of a PD-1 ligand during cell activation has an effect on the expression of several genes. The "PD-1 gene expression profile" may therefore be used in screening methods for the identification of modulators (e.g., inhibitors/antagonists, activators/agonists) of PD-1 activity, which in turn may be used for modulation of immune function/response (e.g., PD-1-mediated immune function), for example for the treatment or prevention of immune conditions such as chronic infections (e.g., viral infection), autoimmune diseases, inflammatory disorders, allergies, transplant rejection, cancer, immune deficiency, and other immune system-related disorders. The "PD-1 gene expression profile" may also be used in diagnostic methods for determining whether a subjects suffers from a disease or condition associated with altered PD-1 activity.

Accordingly, in a first aspect, the present invention provides a method (e.g., an in vitro method) of determining whether a test compound modulates PD-1 activity comprising:
(a) providing an activated immune cell expressing PD-1;
(b) determining a gene expression profile of said immune cell in the presence of said test compound;
(c) comparing said gene expression profile to a corresponding reference gene expression profile determined in the absence of said test compound;
wherein said gene expression profile comprises a candidate expression value for at least two genes, wherein said at least two genes are selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, LTB, MYH9, CLIP3, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAMS, BAZ1A, IL3, FOS, HES4, TIMP1, TNS3, NFKBIA, CGA, TSC22D1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, PLAGL2, KLF2, PRR14, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, BIRC3, TMEM187, C6orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5; and
wherein said reference gene expression profile comprises a reference expression value for said at least two genes; and
(d) determining whether said test compound modulates PD-1 activity based on said comparison.

In an embodiment, the above-mentioned reference expression value corresponds to the level of expression of said at least two genes in the absence of a known modulator (inhibitor or agonist) of PD-1 activity and wherein a difference in said gene expression profile relative to said reference gene expression profile is indicative that said test compound modulates PD-1 activity.

In another embodiment, the above-mentioned reference expression value corresponds to the level of expression of said at least two genes in the presence of an inhibitor of PD-1 activity, and wherein a similarity in said gene expression profile relative to said reference gene expression profile is indicative that said test compound inhibits PD-1 activity.

In another embodiment, the above-mentioned reference expression value corresponds to the level of expression of said at least two genes in the presence of an agonist of PD-1 activity, and wherein a similarity in said gene expression profile relative to said reference gene expression profile is indicative that said compound increases PD-1 activity.

In another aspect, the present invention provides a method (e.g., an in vitro method) for determining whether a test compound inhibits PD-1 activity comprising:
 (a) providing an activated immune cell expressing PD-1;
 (b) determining a gene expression profile of said immune cell in the presence of said test compound;
 (c) comparing said gene expression profile to a corresponding reference gene expression profile determined in the absence of said test compound;
wherein said gene expression profile comprises a candidate expression value for at least two genes, wherein said at least two genes are selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, LTB, MYH9, CLIP3, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAM3, BAZ1A, IL3, FOS, HES4, TIMP1, TNS3, NFKBIA, CGA, TSC22D1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, PLAGL2, KLF2, PRR14, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, BIRC3, TMEM187, C6orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5;
and wherein said reference gene expression profile comprises a reference expression value for said at least two genes; and
 (d) determining whether said compound inhibits PD-1 activity based on said comparison.

In an embodiment, the above-mentioned reference expression value corresponds to the level of expression of said at least two genes in the absence of an inhibitor of PD-1 activity, and wherein a difference in said gene expression profile relative to said reference gene expression profile is indicative that said compound inhibits PD-1 activity.

In an embodiment, the above-mentioned reference expression value corresponds to the level of expression of said at least two genes in the presence of an inhibitor of PD-1 activity, and wherein a similarity in said gene expression profile relative to said reference gene expression profile is indicative that said compound modulates PD-1 activity.

In another aspect, the present invention provides a method for determining whether a test compound induces/increases PD-1 activity comprising:
 (a) providing an activated immune cell expressing PD-1;
 (b) determining a gene expression profile of said immune cell in the presence of said test compound;
 (c) comparing said gene expression profile to a corresponding reference gene expression profile determined in the absence of said test compound;
wherein said gene expression profile comprises a candidate expression value for at least two genes, wherein said at least two genes are selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, LTB, MYH9, CLIP3, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAMS, BAZ1A, IL3, FOS, HES4, TIMP1, TNS3, NFKBIA, CGA, TSC22D1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, PLAGL2, KLF2, PRR14, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, BIRC3, TMEM187, C6orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5;
and wherein said reference gene expression profile comprises a reference expression value for said at least two genes; and
 (d) determining whether said compound increases/induces PD-1 activity based on said comparison.

In an embodiment, the above-mentioned reference expression value corresponds to the level of expression of said at least two genes in the absence of an agonist of PD-1 activity, and wherein a difference in said gene expression profile relative to said reference gene expression profile is indicative that said compound increases PD-1 activity.

In another embodiment, the above-mentioned reference expression value corresponds to the level of expression of said at least two genes in the presence of an agonist of PD-1 activity, and wherein a similarity in said gene expression profile relative to said reference gene expression profile is indicative that said compound increases PD-1 activity.

The present invention further provides a compound (i.e., modulators of PD-1 activity) identified by the above-mentioned method. The present further provides a composition comprising the compound identified by the above-mentioned method and a pharmaceutically acceptable carrier.

The compound (i.e., modulators of PD-1 activity) identified by the above-mentioned method (or the above-mentioned composition) may be used, for example, for preventing and/or treating diseases or conditions associated with PD-1 activity, including autoimmune/inflammatory diseases, transplant rejections and chronic infectious diseases (e.g., HIV infection). Activators or agonists of PD-1 activity may be useful in situations in which PD-1 activity is abnormally low/downregulated, and in which increased PD-1 activity is likely to have a beneficial effect. Likewise, inhibitors of PD-1 activity may be useful in situations in which PD-1 activity is abnormally high/upregulated, and in which decreased PD-1 activity is likely to have a beneficial effect.

Accordingly, the present invention provides a use of a compound identified by the above-mentioned method (or the above-mentioned composition) for preventing or treating a disease or condition associated with altered/aberrant PD-1 activity. The present invention also provides a use of a compound identified by the above-mentioned for the preparation of a medicament for preventing or treating a disease or condition associated with altered/aberrant PD-1 activity. The present invention also provides a compound identified by the above-mentioned (or the above-mentioned composition) for preventing or treating a disease or condition associated with altered/aberrant PD-1 activity. The present invention also provides a compound identified by the above-mentioned for the preparation of a medicament for preventing or treating a disease or condition associated with altered/aberrant PD-1 activity. The present invention also provides a method for preventing or treating a disease or condition associated with altered/aberrant PD-1 activity comprising administrating an effective amount of a compound identified by the above-mentioned method (or the above-mentioned composition) to a subject. In embodiments, the term "subject" is meant to refer to any mammal including human, mice, rat, dog, cat, pig, monkey, horse, etc. In a particular embodiment, it refers to a human.

In another aspect, the present invention provides a method (e.g., an in vitro method) of determining whether a subject suffers from a disease or condition associated with altered PD-1 activity, said method comprising:
  (a) providing a sample comprising activated immune cells from said subject;
  (b) contacting said sample with a ligand for PD-1;
  (c) determining a gene expression profile of said sample;
  (d) comparing said gene expression profile to a corresponding reference gene expression profile;
wherein said gene expression profile comprises a candidate expression value for at least two genes, wherein said at least two genes are selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, LTB, MYH9, CLIP3, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAM3, BAZ1A, IL3, FOS, HES4, TIMP1, TNS3, NFKBIA, CGA, TSC22D1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, PLAGL2, KLF2, PRR14, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, BIRC3, TMEM187, C6orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5;
and wherein said reference gene expression profile comprises a reference expression value for said at least two genes; and
  (e) determining whether said subject suffers from a disease or condition associated with altered PD-1 activity based on said comparison.

In embodiments, the above-noted at least two genes are selected from genes who are members of the TNFSF and TNFRSF (e.g., CD27 [SEQ ID NOs: 329/330], TNFSF14 [SEQ ID NOs: 135/136; 137/138], CD70 [SEQ ID NOs: 29/30; also known as CD27L] and ICOS [SEQ ID NOs: 485/486]), cytokines and genes of the KLF (e.g., KLF2 [SEQ ID NOs: 353/354] and KLF6 [SEQ ID NOs: 71/72; 73/74]) family.

In an embodiment, the above-mentioned reference expression value corresponds to the level of expression of said at least two genes in a control sample obtained from a subject known not to suffer from a disease or condition associated with altered PD-1 activity, and wherein a difference in said gene expression profile relative to said reference gene expression profile is indicative that subject suffers from a disease or condition associated with altered PD-1 activity.

In another embodiment, the above-mentioned reference expression value corresponds to the level of expression of said at least two genes in a control sample obtained from a subject suffering from a disease or condition associated with altered PD-1 activity, and wherein a similarity in said gene expression profile relative to said reference gene expression profile is indicative that subject suffers from a disease or condition associated with altered PD-1 activity.

The term "gene expression profile" or "expression profile" of a biological sample refers to a set of values representing nucleic acid (e.g., mRNA, a cDNA derived from a mRNA) or polypeptide levels corresponding to one or more genes in the cell/sample. An expression profile may comprise, for example, values representing expression levels of at least about 2 genes, at least about 3 genes, at least about 4 genes, at least about 5 genes, at least about 10 genes, at least about 20 genes or at least about 50, 100, 200 or more genes. The expression level of a gene may be determined by the amount of nucleic acid (e.g., DNA, RNA) or protein present in the sample which corresponds to the gene. The gene expression profile therefore, may include levels of DNA, RNA and/or protein correlated to specific genes within the sample.

In the screening method of the invention, a "first" gene expression profile is determined in a cell sample (e.g., an immune cell sample) incubated in the presence of a test compound. In the methods of the invention, the "first" gene expression profile may be compared to a corresponding "reference" gene expression profile in order to determine whether the test compound modulates (inhibits and/or increases) PD-1 activity.

Such a reference gene expression profile comprises reference expression values for at least two of the genes noted herein. A reference expression value for a set of genes may be determined, for example, by determining the expression level of these genes following incubation of a cell sample in the absence of a modulator (an inhibitor or agonist) of PD-1 activity. Alternatively, a reference expression value for a set of genes may be determined, for example, by determining the expression level of these genes following incubation of a cell sample in the presence of a known inhibitor or activator (e.g., agonist) of PD-1 activity. Comparison of a reference expression profile to a "first" expression profile (i.e., a profile determined in a sample in the presence of a test compound) may be used to determine whether the test compound modulates PD-1 activity. For example, if a profile determined in the presence of a test compound is similar to a reference profile determined in the presence of a known inhibitor of PD-1 activity, it is indicative that the test compound inhibits PD-1 activity. A reference expression value for a set of genes may also be determined, for example, by determining the expression level of these genes following incubation of a cell sample in the absence of the test compound.

In the method of diagnosis of the invention, a "first" gene expression profile is determined in a cell sample (e.g., an immune cell sample) obtained from a first subject. In the methods of the invention, the "first" gene expression profile may be compared to a corresponding "reference" gene expression profile in order to determine whether the first subject suffers from a disease or condition associated with PD-1 activity.

Such a reference gene expression profile comprises reference expression values for at least two of the genes noted herein. A reference expression value for a set of genes may be determined, for example, by determining the expression level of these genes following incubation of a cell sample obtained from a healthy subject (i.e., known to not suffer from a disease or condition associated with PD-1 activity), or obtained from the first subject at an earlier time. Alternatively, a reference expression value for a set of genes may be determined, for example, by determining the expression level of these genes in a cell sample obtained from a subject known to suffer from a disease or condition associated with PD-1 activity. Comparison of a reference expression profile to a "first" expression profile (i.e., a profile determined in a sample from a first subject to be diagnosed) may be used to determine whether the subject suffers from a disease or condition associated with PD-1 activity. For example, if a profile determined in the first is similar to a reference profile determined in a healthy subject, it is indicative that the first subject suffers from a disease or condition associated with PD-1 activity.

The above-mentioned method may also be used to determine whether a subject is at risk for a disease or condition associated with altered/aberrant PD-1 activity. As such, administration of a prophylactic agent can occur prior to the manifestation of symptoms characteristic of aberrant or altered PD-1 activity, such that a disease or condition is prevented or, alternatively, delayed in its onset or progression.

The above-mentioned method may also be used for prognostication of a disease or condition associated with altered/aberrant PD-1 activity, to determine if there is an improvement or a worsening of the severity/progression/symptoms of the disease or condition over time.

As used herein, a "similarity" in gene expression profiles refers to a gene expression profile, which when compared to a corresponding reference profile (i.e., comparison of expression of the at least two genes of the gene profile with the expression of the corresponding at least two genes of the reference profile) exhibits a difference in expression level of less than about 50%, in further embodiments of less than about 40%, 30%, 20%, 15%, 10%, or 5%. In cases where a gene expression profile comprises expression levels of a plurality of genes, preferably more than about 50%, in further embodiments more than about 60%, 70% or 80%, of the genes, when their expression levels are compared as noted above, exhibit a difference in expression level of less than about 50%, in further embodiments less than about 40%, 30%, 20%, 15%, 10%, or 5%.

As used herein, a "difference" in gene expression profile refers to a gene expression profile, which when compared to a corresponding reference profile (i.e., comparison of expression of each of the one or more genes of the gene profile with the expression of the corresponding one or more genes of the reference profile) exhibits a difference in expression level of at least about 50% (1.5-fold), in further embodiments at least about 60%, 70%, 80%, 90%, or 100% (2-fold). In cases where a gene expression profile comprises expression levels of a plurality of genes, preferably more than about 50%, in further embodiments more than about 60%, 70% or 80%, of the genes, when their expression levels are compared as noted above, exhibit a difference in expression level of at least about 50% (1.5-fold), in further embodiments at least about 60%, 70%, 80%, 90%, or 100% (2-fold).

The term "PD-1 activity" (or "PD-1-mediated immune modulation") as used herein refers to one or more immunoregulatory activities associated with PD-1, such as the modulation of an activation or inhibitory signal in an activated immune cell (e.g., a T cell, a $CD4^+$ or $CD8^+$ T cell) and/or the modulation of proliferation and/or cytokine secretion by an immune cell.

In an embodiment, the level of expression of the above-mentioned gene(s) is determined by determining the level of expression of one or more nucleic acid(s) or polypeptide(s) encoded thereby set forth in Table II. In another embodiment, the level of expression of the above-mentioned gene(s) is determined by determining the level of expression of one or more nucleic acid(s) or polypeptide(s) encoded thereby comprising a sequence selected from SEQ ID NOs: 1-492 (odd SEQ ID NOs: represent nucleic acid/nucleotide sequences, even numbers represent polypeptide/amino acid sequences).

In further embodiments, the invention relates to the use of nucleic acid(s) (e.g., a probe(s)) which is substantially identical or substantially complementary (e.g., for hybridization under suitable conditions) to a nucleic acid sequence selected from the group consisting of nucleic acid sequences among SEQ ID NOs: 1-492 (odd numbers represent nucleic acid sequences), a complement thereof, or a portion thereof, in the methods, products, uses, kits and collections described herein.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid or polypeptide sequence is "homologous" to another sequence if the two sequences are substantially identical and the functional activity of the sequences is conserved (as used herein, the term 'homologous' does not infer evolutionary relatedness). Two nucleic acid or polypeptide sequences are considered "substantially identical" if, when optimally aligned (with gaps permitted), they share at least about 50% sequence similarity or identity and/or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with a nucleic acid sequence or polypeptide amino acid sequence described herein, e.g., any of SEQ ID NOs: 1-492. "Substantially complementary" nucleic acids are nucleic acids in which the complement of one molecule is substantially identical to the other molecule.

Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BEST-FIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably highly stringent, conditions. Hybridisation to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under high stringency conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

In an embodiment, it is desirable to amplify the nucleic acid sample prior to hybridization. One of skill in the art will appreciate that whatever amplification method is used, if a quantitative result is desired, a method is used that maintains or controls for the relative frequencies of the amplified nucleic acids to achieve quantitative amplification. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. For example, a high-density array may then include probes specific to the internal standard for quantification of the amplified nucleic acid. Other suitable amplification methods include, but are not limited to polymerase chain reaction (PCR) Innis, et al., PCR Protocols. A guide to Methods and Application. Academic Press, Inc. San Diego, (1990)), ligase chain reaction (LCR) (see Wu and Wallace, Genomics, 4: 560, Landegren, et al., Science, 241: 1077 and Barringer, et al., Gene, 89: 117), transcription amplification (Kwoh, et al., Proc. Natl. Acad. Sci. USA, 86: 1173), and self-sustained sequence replication (Guatelli, et al, Proc. Nat. Acad. Sci. USA, 87: 1874).

The analysis of the expression of a plurality of genes of the present invention may be carried out separately or simultaneously with one test sample.

Expression levels may in general be detected by either detecting mRNA from the cells and/or detecting expression products, such as polypeptides and proteins. Expression of the transcripts and/or proteins encoded by the nucleic acids described herein may be measured by any of a variety of known methods in the art. In general, the nucleic acid sequence of a nucleic acid molecule (e.g., DNA or RNA) in a cell sample can be detected by any suitable method or technique of measuring or detecting gene sequence or expression. Such methods include, but are not limited to, polymerase chain reaction (PCR), reverse transcriptase-PCR (RT-PCR), in situ PCR, quantitative PCR (q-PCR), in situ hybridization, Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization; and detection of a reporter gene. The term "quantifying" or "quantitating" when used in the context of quantifying transcription levels of a gene can refer to absolute or to relative quantification. Absolute quantification may be accomplished by inclusion of known concentration(s) of one or more target nucleic acids and referencing the hybridization intensity of unknowns with the known target nucleic acids (e.g., through generation of a standard curve). Alternatively, relative quantification can be accomplished by comparison of hybridization signals between two or more genes, or between two or more treatments to quantify the changes in hybridization intensity and, by implication, transcription level.

Methods to measure protein expression levels of selected genes of this invention are well known in the art. Examples of such methods include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, and assays based on a property of the protein including but not limited to DNA binding, ligand binding, or interaction with other protein partners.

Expression levels may be represented by any form of data which is suitable for use in the methods (e.g., comparisons and assessments) described herein. In embodiments, such data may be recorded on a computer-readable medium.

Methods for normalizing the level of expression of a gene are well known in the art. For example, the expression level of a gene of the present invention can be normalized on the basis of the relative ratio of the mRNA level of this gene to the mRNA level of a housekeeping gene or the relative ratio of the protein level of the protein encoded by this gene to the protein level of the housekeeping protein, so that variations in the sample extraction efficiency among cells or tissues are reduced in the evaluation of the gene expression level. A "housekeeping gene" is a gene the expression of which is substantially the same from sample to sample or from tissue to tissue, or one that is relatively refractory to change in response to external stimuli. A housekeeping gene can be any RNA molecule other than that encoded by the gene of interest that will allow normalization of sample RNA or any other marker that can be used to normalize for the amount of total RNA added to each reaction. For example, the GAPDH gene, the G6PD gene, the ACTIN gene, ribosomal RNA, 36B4 RNA, PGK1, RPLP0, or the like, may be used as a housekeeping gene.

Methods for calibrating the level of expression of a gene are well known in the art. For example, the expression of a gene can be calibrated using reference samples, which are commercially available. Examples of reference samples include, but are not limited to: Stratagene® QPCR Human Reference Total RNA, Clontech™ Universal Reference Total RNA, and XpressRef™ Universal Reference Total RNA.

Nucleic acid arrays may be used for detecting the expression of the genes (e.g. for determining a gene expression profile) of the present invention. The production and application of high-density arrays in gene expression monitoring have been disclosed previously in, for example, PCT Publication No. WO 97/10365; PCT Publication No. WO 92/10588; U.S. Pat. No. 6,040,138; U.S. Pat. No. 5,445,934; or PCT Publication No. WO 95/35505, all of which are incorporated herein by reference in their entireties. Also for examples of arrays, see Hacia et al., Nature Genetics 14: 441; Lockhart et al., Nat. Biotechnol. 14:1675-1680; and De Risi et al., Nature Genetics 14: 457, each of which is incorporated by reference in its entirety. In general, in an array, an oligonucleotide, a cDNA, or genomic DNA, that is a portion of a known gene, occupies a known location on a substrate. A nucleic acid target sample is hybridized with an array of such oligonucleotides and then the amount of target nucleic acids hybridized to each probe in the array is quantified. One quantifying method is to use confocal microscope and fluorescent labels. The Affymetrix GeneChip™ Array system (Affymetrix, Santa Clara, Calif.), the Atlas™ Human cDNA Expression Array system and the Illumina™ gene expression Array system are suitable for quantifying the hybridization; however, it will be apparent to those of skill in the art that any similar systems or other effectively equivalent detection methods can also be used. In a particularly preferred embodiment, one can use the knowledge of the genes described herein to design novel arrays of polynucleotides, cDNAs or genomic DNAs for screening methods described herein. Such novel pluralities of polynucleotides are contemplated to be a part of the present invention and are described in detail below.

Suitable nucleic acid samples for screening on an array contain transcripts of interest or nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like. In an embodiment, such a sample is a total RNA preparation of a biological sample (e.g., peripheral blood mononuclear cells or PBMCs, immune cells, immune cell subpopulations). In another embodiment, such a nucleic acid sample is the total mRNA isolated from such a biological sample.

Methods of isolating total mRNA are well known to those of skill in the art. In one embodiment, the total nucleic acid is isolated from a given sample using, for example, an acid guanidinium-phenol-chloroform extraction method and polyA and mRNA is isolated by oligo dT column chromatography or by using (dT)n magnetic beads (see, e.g., Sambrook et al., Molecular Cloning: A Laboratory Manual ($2^{nd}$ ed.), Vols. 1-3, Cold Spring Harbor Laboratory, (1989), or Current Protocols in Molecular Biology, F. Ausubel et al., ad. Greene Publishing and Wiley-Interscience, New York (1987)).

In an embodiment, the above-mentioned gene expression profile is determined after between about 20 to about 40 minutes (e.g., after about 30 minutes) of activation, and the above-mentioned gene expression profile comprises a candidate expression value for at least two genes selected from FAM65A, E4F1, CBFA2T3, CENPE, SPEN, TNF, BAT2D1, SPTBN1, BRD2, CCAR1, RPL7L1, MIDN, VHL, PCNT, RUNX3, TJAP1, MACF1, MYH9, CLIP3, SNX26, CDK5RAP2, BAZ1A, FOS, EIF4G3, DUSP1, SLC9A1, MEF2D, SNAPC4, SRRM2, KLF2, PRR14, BHLHB2, PPP1R15A, AUTS2, SETD2, CENPF, FOSB, EGR2, PHACTR4, ULK1, GNL3L, ZCCHC6, ITPR3, ZFP36, NOTCH1, POLE and EGR4.

In another embodiment, the above-mentioned gene expression profile is determined after between about 2 to about 4 hours (e.g., after about 3 hours) of activation, and the above-mentioned gene expression profile comprises a candidate expression value for at least two genes selected from E4F1, CBFA2T3, MT1A, ANKRD5, KLF6, SPEN, TNF, BAT2D1, ZYX, SPTBN1, SLA, SOCS1, OSGIN1, BRD2, VGF, TNFSF14, RPL28, CSF2, CCAR1, RPL7L1, MIDN, LUZP1, VHL, PCNT, SPRY1, RUNX3, RDH10, DDEF1, GZMB, TJAP1, MACF1, JMJD1C, MYH9, CLIP3, SNX26, TAGAP, FAM50A, CDK5RAP2, TAF1C, KIAA1754, SUPT6H, SH2D2A, ATP6V0A4, TNFRSF8, ITGA5, IL3, TIMP1, SLC9A1, MEF2D, SNAPC4, DPP9, SRRM2, CD69, IRX5, PLAGL2, KLF2, PRR14, FSCN1, LTBP4, USP11, BHLHB2, ARC, PPP1R15A, AUTS2, MARVELD3, SETD2, CENPF, CBX6, ULK1, GNL3L, ZCCHC6, ITPR3, MT2A, NFATC1, ZFP36, BCL9, NOTCH1, POLE, CREBBP, ACVR1, ICOS and MAG1.

In another embodiment, the above-mentioned gene expression profile is determined after between about 4 to about 8 hours (e.g., after about 6 hours) of activation, and the above-mentioned gene expression profile comprises a candidate expression value for at least two genes selected from CD55, DIP, STS-1, CD70, BACH2, REL, KIAA0831, CBFA2T3, KLF6, SMOX, FBXO34, LZTS1, LAMP3, SPEN, SH2B3, ATP1B1, SLA, PLAU, SOCS1, BRD2, PTPN6, TNFSF14, CD97, CSF2, CD83, SPRY1, RUNX3, MBP, RDH10, LTB, MYH9, CCDC64, TAGAP, TRAF1, LRRC8C, IL23A, SH2D2A, IL21R, MAPRE2, TMEM158, IL3, FOS, TNS3, NFKBIA, TSC22D1, ATP6V1B2, DUSP1, SLC9A1, GPR171, CD27, TNFRSF21, TBC1D10C, LTBP4, MARVELD3, ADORA2A, CCL4L1, PTPN22, PRKCH, BIRC3, C6orf190, ADM, EOMES, POU2AF1, NFATC1, LY96, ACVR1, MYC, CCL1, CXCR3, MAG1 and FXYD5.

In another embodiment, the above-mentioned gene expression profile is determined after about 18 hours (e.g., between about 12 to about 24 hours) of activation, and the above-mentioned gene expression profile comprises a candidate expression value for at least two genes selected from CD55, NFKB2, TPST2, CST7, GNG4, CD70, REL, PAM, KIAA0831, LOC197322, IL2RA, IL13, CBFA2T3, KRT1, MT1A, NQO1, FBXO34, LAMP3, TNFSF14, IL2, CD97, CSF2, CD83, BCL2L1, CCL20, SPRY1, BCL2A1, MBP, RHOU, RDH10, HTR2B, GZMB, RCBTB2, RGS16, LTB, GBE1, CCDC64, PHEX, TAGAP, TRAF1, CDK5RAP2, LRRC8C, IL23A, SH2D2A, IL21R, ATP6V0A4, ITGA5, JAM3, IL3, HES4, TNS3, NFKBIA, CGA, ATP6V1B2, GPR171, CD27, ALDOC, METT11D1, CD69, PLAGL2, KLF2, BIRC3, IGFBP2, RXRA, ARG2, CENPF, ADORA2A, LAIR2, PTPN22, GNL3L, MFSD2, TMEM187, C6orf190, ADM, POU2AF1, C1orf165, PFKFB4, NR4A2, CCL1 and ICOS.

In an embodiment, the above-mentioned reference gene expression profile is contained within a database. As used herein the term "database" or "gene expression database" refers to the expression profiles for a given sample type or types. A plurality of gene expression profiles may be used to generate the gene expression database. The gene expression profiles are statistically analysed to identify gene expression levels that characterise particular sample types (e.g., a sample associated with inhibition or stimulation of PD-1).

In another embodiment, the above-mentioned comparing is carried out using a computer algorithm. Examples of well-known algorithms includes linear or nonlinear regression algorithms; linear or nonlinear classification algorithms; ANOVA; neural network algorithms; genetic algorithms; support vector machines algorithms; hierarchical analysis or clustering algorithms; hierarchical algorithms using decision trees; kernel based machine algorithms such as kernel partial least squares algorithms, kernel matching pursuit algorithms, kernel fisher discriminate analysis algorithms, or kernel principal components analysis algorithms; Bayesian probability function algorithms; Markov Blanket algorithms; recursive feature elimination or entropy-based recursive feature elimination algorithms; a plurality of algorithms arranged in a committee network; and forward floating search or backward floating search algorithms.

The gene expression profiles useful for the method of the invention (e.g., a reference expression profile) can be provided on an electronic media that can be automatically read such as computer readable media (magnetic, optical, and the like). This media can be part of a kit that can also include instructions for assessing the gene expression profiles in such media. For example, the kit may comprise a CD-ROM having computer instructions for comparing gene expression profiles of the portfolios of genes described above. The kit may also have gene expression profiles (e.g., a reference gene expression profile) digitally recorded therein so that they may be compared with gene expression data from subject samples (e.g., candidate transplant donors). The kit may also comprise a data analysis tool (e.g., a computer program) that permits the comparison of gene expression profiles.

In an embodiment, the above-mentioned immune cell is a T cell (e.g., a primary T cell or an immortalized T cell such as a T cell line/hybridoma). In a further embodiment, the above-mentioned T cell is a $CD4^+$ T cell. In a further embodiment, the above-mentioned $CD4^+$ T cell is a Jurkat $CD4^+$ T cell or a primary human $CD4^+$ T cell. In another embodiment, the above-mentioned cell is capable of expressing PD-1 (e.g., upon induction) or expresses PD-1 (e.g., native or recombination expression). The above-mentioned cell may be prepared for example by transfecting/transforming an immune cell with a nucleic acid encoding PD-1 or a fragment thereof having PD-1 activity.

In an embodiment, the above-mentioned method further comprises activation of the immune cell (e.g., a T cell).

The term "activation" or "stimulation" is generally defined to refer to any change induced in the basal or resting state of an immune cells (e.g., a T cell). This includes, but is not limited to, increased cell proliferation and DNA synthesis, cytokine/chemokine and cytotoxic molecule production/secretion, rise in intracellular calcium, release of water soluble inositol phosphates, increased IL-2 receptor and/or CD69 expression, enhanced proliferative response to IL-2. An "activated immune cell" is an immune cell that has undergone or been subjected to such activation.

Methods and reagents for activating/stimulating T cells are well known in the art. For example, T cells can be stimulated using chemical agents, such as activators of protein kinase C (e.g., phorbol 12-myristate 13-acetate (PMA)) in combination with a calcium ionophore (e.g., ionomycin), mitogens (e.g., phytohaemagglutinin (PHA)), ligands (e.g., antibodies, natural or synthetic ligands) of the T cell receptor (TCR) and/or of co-stimulatory/accessory molecule(s) (e.g., CD2, CD28, 4-1BB). Examples of ligands of the TCR include antigenic peptides, superantigens, antibodies (or antigenic fragments thereof) directed against the TCR/CD3 complex (e.g., the α and/or β chain(s) or CD3 chains). In an embodiment, the above-mentioned activation/stimulation is performed using a ligand of the T-cell receptor and of a co-stimulatory molecule. In a further embodiment, the above-mentioned activation is performed using a first antibody, or a fragment thereof, directed against CD3 (e.g., OKT3) and a second antibody, or a fragment thereof, directed against CD28. T cell stimulation may further be performed in the presence of other agents including cytokines (e.g., IL-2), chemokines and/or growth factors, for example. In another embodiment, the above-mentioned stimulation is performed in the presence of a PD-1 agonist/ligand (e.g., an anti-PD-1 antibody, PD-L1 and/or PD-L2). Such agonist/ligand may be soluble, coated on a support, or expressed at the surface of a cell, for example.

In an embodiment, the above-mentioned method comprises determining the expression value of at least 3 genes. In another embodiment, the above-mentioned method comprises determining the expression value of at least 4 genes. In another embodiment, the above-mentioned method comprises determining the expression value of at least 5 genes. In another embodiment, the above-mentioned method comprises determining the expression value of at least 6 genes. In another embodiment, the above-mentioned method comprises determining the expression value of at least 7 genes. In another embodiment, the above-mentioned method comprises determining the expression value of at least 8 genes. In another embodiment, the above-mentioned method comprises determining the expression value of at least 9 genes. In another embodiment, the above-mentioned method comprises determining the expression value of at least 10 genes. In another embodiment, the above-mentioned method comprises determining the expression value of at least 15 genes. In another embodiment, the above-mentioned method comprises determining the expression value of at least 20 genes. In another embodiment, the above-mentioned method comprises determining the expression value of at least 25 genes. In another embodiment, the above-mentioned method comprises determining the expression value of at least 50 genes. In another embodiment, the above-mentioned method comprises determining the expression value of at least 100 genes. In another embodiment, the above-mentioned method comprises determining the expression of all the above-mentioned genes.

The screening methods mentioned herein may be employed either with a single test compound or a plurality or library (e.g., a combinatorial library) of test compounds. In the latter case, synergistic effects provided by combinations of compounds may also be identified and characterized. The above-mentioned compounds may be used for prevention and/or treatment of immune-related diseases (e.g., infections, inflammatory/autoimmune diseases), or may be used as lead compounds for the development and testing of additional compounds having improved specificity, efficacy and/or pharmacological (e.g., pharmacokinetic) properties. In an embodiment the compound may be a prodrug which is altered into its active form at the appropriate site of action (e.g., in lymph nodes, in infected or inflamed organs/tissues). In certain embodiments, one or a plurality of the steps of the screening/testing methods of the invention may be automated.

In another aspect, the present invention provides a kit comprising a collection of two or more isolated nucleic acids, their complements, or portions thereof, wherein said two or more nucleic acids correspond to nucleotide sequences of two or more genes selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, LTB, MYH9, CLIP3, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAM3, BAZ1A, IL3, FOS, HES4, TIMP1, TNS3, NFKBIA, CGA, TSC22D1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, PLAGL2, KLF2, PRR14, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, BIRC3, TMEM187, C6orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5, together with instructions setting forth the above-mentioned method of determining whether a test compound inhibits or stimulates PD-1 activity.

The above-mentioned kit may comprise, for example, a first nucleic acid (or a complement or portion thereof) comprising/corresponding to a nucleotide sequence from a first gene and a second nucleic acid (or a complement or portion thereof) comprising/corresponding to a nucleotide sequence from a second gene. As such, the above-mentioned kit comprising said two or more nucleic acids (or complements or portions thereof) may be used, for example, to simultaneously determine the expression of two or more genes listed above.

In another aspect, the present invention provides a kit or package comprising:

(a) a collection of two or more oligonucleotides that hybridize under high stringency conditions to one or more nucleotide sequences of at least two genes selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, LTB, MYH9, CLIPS, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAM3, BAZ1A, IL3, FOS, HES4, TIMP1, TNS3, NFKBIA, CGA, TSC22D1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, PLAGL2, KLF2, PRR14, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, BIRC3, TMEM187, C6 orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5, or to a complement thereof; or (b) a collection of two or more reagents that specifically binds to polypeptides encoded by said at least two genes; together with instructions setting forth the above-mentioned method of determining whether a test compound inhibits or stimulates PD-1 activity.

In embodiments, the above-noted at least two genes are selected from genes who are members of the TNFSF and TNFRSF (e.g., CD27 [SEQ ID NO: 329], TNFSF14 [SEQ ID NOs: 135; 137], CD70 [SEQ ID NO: 29; also known as CD27L] and ICOS [SEQ ID NO: 485]), cytokines and genes of the KLF (e.g., KLF2 [SEQ ID NO: 353] and KLF6 [SEQ ID NOs: 71; 73]) family.

The above-mentioned kit may comprises (1) a first oligonucleotide that hybridizes under high stringency conditions to one or more nucleotide sequence(s) from a first gene (or a complement thereof) and (2) a second oligonucleotide that hybridize under high stringency conditions to one or more nucleotide sequence(s) from a second gene (or a complement thereof). The above-mentioned kit may alternatively or further comprise (1) a first reagent that specifically binds to a polypeptide encoded by a first gene and (2) a second reagent that specifically binds to a polypeptide encoded by a second gene. As such, the above-mentioned kit comprising said two or more oligonucleotides or said two or more reagents may be used, for example, to simultaneously determine the expression of two or more genes listed above.

In an embodiment, the above-mentioned nucleic acids or nucleotides sequences comprise a nucleotide sequence selected from SEQ ID NOs: 1-492 (odd numbers), or complements thereof.

In another embodiment, the above-mentioned two or more oligonucleotides are: (a) two or more oligonucleotides comprising a nucleotide sequence selected from SEQ ID NOs: 493-671; a complement of the two or more oligonucleotides of (a); a fragment of (a) or (b).

In another embodiment, the above-mentioned polypeptides comprise an amino acid sequence selected from the group consisting of SEQ ID NOs: 1-492 (even numbers).

An "oligonucleotide" is meant to include a nucleic acid (e.g., a probe or primer) that hybridizes specifically to a target sequence in a nucleic acid or its complement, under conditions that promote hybridization, thereby allowing detection of the target sequence or its amplified nucleic acid. Detection may either be direct (i.e., resulting from a probe hybridizing directly to the target or amplified sequence) or indirect (i.e., resulting from a probe hybridizing to an intermediate molecular structure that links the probe/primer to the target or amplified sequence). A probe's or primer's "target" generally refers to a sequence within a nucleic acid sequence (i.e., a subset of the sequence) that hybridizes specifically to at least a portion of the probe/primer sequence by standard hydrogen bonding or "base pairing." Sequences that are "sufficiently complementary" allow stable hybridization of a probe/primer sequence to a target sequence, even if the two sequences are not completely complementary. A probe/primer may be labelled or unlabeled. In an embodiment, the oligonucleotide (or a fragment thereof) comprises at least 10 nucleotides, in further embodiments at least 11, 12, 13, 14, 15, 16, 17, 18, 19, 20, 21, 22, 23, 24, 25, 30, 35, 40, 45 or 50 nucleotides. In an embodiment, the oligonucleotide comprises from about 10 to about 100 nucleotides. In further embodiments from about 12 to about 80, from about 15 to about 50 nucleotides, from about 20 to about 40, from about 25 to about 30 nucleotides. In another embodiment, the oligonucleotide comprises about 50 nucleotides.

Hybridization under high stringency conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). High stringency conditions may be those in which the salt concentration is less than approximately 1.5 M Na ion, typically about 0.01 to 1.0 M Na ion (or other salts) at pH 7.0 to 8.3 and the temperature is at least about 30° C., and generally at least about 50° C. to 60° C. High stringency conditions also may be achieved with the addition of destabilizing agents such as formamide. Another example of high stringency conditions include hybridization in 50% formamide, 1M NaCl, 1% SDS at 37° C., and a wash in 0.1×SSC at 60 to 65° C. Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point (Tm) for the specific sequence at a defined ionic strength and pH.

In an embodiment, the above-mentioned oligonucleotides (e.g., probes) or nucleic acids, or complements thereof, are hybridizable elements on an array (e.g., bound at a known position), and as such can hybridize to gene products (e.g., cDNAs, mRNA) of the present invention. In one embodiment of the invention, the array is a matrix in which each position represents a discrete binding site for a product encoded by a gene of the genes listed in Table II.

As used herein, a reagent which specifically binds with the polypeptide generally refers to chemical agents, or natural products, or antibodies, or antigen binding fragments thereof, e.g., for the detection of the expression of genes of interest. In embodiments, the reagent comprises chemical agents, or natural products, or antibodies, or antigen binding fragments thereof, that selectively bind to proteins encoded by genes that are regulated in cells, and that can be detected as protein products using antibodies. In addition, the reagent comprises chemical agents, or natural products, or antibodies, or antigen binding fragments thereof, that selectively bind to proteins or portions thereof (peptides) encoded by at least two genes selected from SEQ ID NOs: 1-492 (even numbers represent polypeptide sequences). In an embodiment, the above-mentioned reagent consists of at least two antibodies, antigen binding fragments thereof, or antigen binding peptides, each of which selectively binds to a protein encoded by a gene comprising, or expressing a transcript comprising, at least two nucleic acid sequences selected from the group consisting of SEQ ID NOs: 1-492.

According to the present invention, the phrase "selectively binds to" refers to the ability of a chemical agent, a natural product, an antibody, antigen-binding fragment or binding partner (antigen binding peptide) to preferentially bind to specified proteins. More specifically, the phrase "selectively binds" refers to the specific binding of one protein to another molecule (e.g., chemical agent, natural product, an antibody, fragment thereof, or binding partner to an antigen), wherein the level of binding, as measured by any standard assay (e.g., an immunoassay, fluorescence), is statistically significantly higher than the background control for the assay. For example, when performing an immunoassay, controls typically include a reaction well/tube that contain chemical agent, natural product, antibody or antigen binding fragment alone (i.e., in the absence of antigen), wherein an amount of reactivity (e.g., non-specific binding to the well) by the chemical agent, natural product, antibody or antigen binding fragment thereof in the absence of the antigen is considered to be background. Binding can be measured using a variety of methods standard in the art including enzyme immunoassays (e.g., fluorescence, ELISA, immunoblot assays, etc.).

For screening or diagnostic applications, the reagent (i.e., the antibodies or antigen binding fragments thereof) is either in a free state or immobilized on a solid support, such as a tube, a bead, a microarray or any other conventional support used in the field. Immobilization is achieved using direct or indirect means. Direct means include passive adsorption (non-covalent binding) or covalent binding between the support and the reagent. By "indirect means" is meant that an anti-reagent compound that interacts with a reagent is first attached to the solid support. Indirect means may also employ a ligand-receptor system, for example, where a molecule such as a vitamin is grafted onto the reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail. The reagent is labeled with a detection means which allows for the detection of the reagent when it is bound to its target. The detection means may be a fluorescent agent such as fluorescein isocyanate or fluorescein isothiocyanate (FITC), or an enzyme such as horseradish peroxidase or luciferase or alkaline phosphatase, or a radioactive element such as $^{125}$I or $^{51}$Cr.

The above-mentioned kits may further provide substances useful as standard (e.g., a sample containing a known quantity of a nucleic acid/polypeptide to which test results can be compared, with which one can assess factors that may alter the readout of a diagnostic test, such as variations in an enzyme activity or binding conditions). Kits for assessing nucleic acid expression may further include other reagents useful in assessing levels of expression of a nucleic acid (e.g., buffers and other reagents for performing PCR reactions, or for detecting binding of a probe to a nucleic acid. Kits may also provide instructions (e.g., instructions for performing the assay and/or interpreting the results), containers, computer readable media (comprising, for example, a data analysis program, a reference gene expression profile, etc.), control samples, and other reagents for obtaining and processing samples for analysis.

In an embodiment, the above-mentioned kit may be used in a screening assay for determining whether a test compound modulates PD-1 activity.

As used herein, disease or condition associated with PD-1 activity generally refers to immunological disorders in which altered PD-1 activity is observed/detected, including autoimmune/inflammatory diseases, transplant rejections and chronic infectious diseases (e.g., HIV infection/AIDS).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The articles "a," "an" and "the" are used herein to refer to one or to more than one (i.e., to at least one) of the grammatical object of the article. The following examples are illustrative of various aspects of the invention, and do not limit the broad aspects of the invention as disclosed herein.

MODE(S) FOR CARRYING OUT THE INVENTION

The present invention is illustrated in further details by the following non-limiting examples.

Example 1

Material and Methods

Preparation of Beads Coated with Antibodies.

The following dilutions of antibodies (Abs) in pure PBS were prepared under sterile conditions and kept at 4° C.: 1/20 of anti-CD3 (BD Pharmingen 0.5 mg/ml Cat. #555330)=10 µl Abs+190 µl PBS; 1/20 of anti-CD28 (BD Pharmingen 0.5 mg/ml Cat. #555726)=10 µl Abs+190 µl PBS; 1/10 of 2.5 mg/ml of anti-PD-1 (clone J105, MBL International, cat. #14-2799)=20 µl Abs+180 µl PBS; Neat 1 mg/ml IgG1 isotype antibody (Sigma #M9269—1 mg). The following antibody mixtures were then prepared:

TABLE I

| | "stimulation" beads CD3:CD28 | "PD-1" beads CD3:CD28:PD-1 | "Isotype" beads CD3:CD28:IgG1 isotype |
|---|---|---|---|
| Antibody mixtures for preparation of beads | | | |
| 1/20 of anti-CD3 | 50 µl | 50 µl | 50 µl |
| 1/20 of anti-CD28 | 10 µl | 10 µl | 10 µl |
| 1/10 of anti-PD-1 | — | 5 µl | — |
| Neat IgG1 | — | — | 1 µl |

The above antibody mixtures were mixed with 50 µl of well-resuspended Dynal CELLcept™ Pan mouse Ig beads (InVitrogen, Cat. # 115.31 D), and incubated under continuous agitation at 4° C. for 1 hour. After 1 hour, 500 µl of PBS supplemented with 0.1% of fetal calf serum (FCS) (0.1% FCS/PBS) was added to each tube and incubation was continued for 30 min. Beads were collected by brief centrifugation and washed with 1 ml of 0.1% FCS/PBS, followed by another centrifugation to collect the beads. This washing step was repeated, and the beads were the resuspended in 500 µl of 0.1% FCS/PBS and stored at 4° C. until use.

Isolation of Primary CD4$^+$ T Cells.

Primary human CD4$^+$ T cells were isolated from total peripheral blood mononuclear cells (PBMCs) obtained from healthy or HIV-1-infected subjects by negative selection using the CD4$^+$ T Cell Isolation Kit™ II (Miltenyi Biotec, Cat. #130-091-155). Cells were rested for 2 h before performing the assays.

Assessment of IL-2 Secretion.

T cells (1-2×10$^6$ isolated primary CD4$^+$ T cells or Jurkat T cells expressing PD-1) were incubated with 100 µl to 200 µl of beads either uncoated or coated with monoclonal antibodies against human CD3 (BD Biosciences, Cat. #555330), CD28 (BD Biosciences, Cat. #348040) and either PD-1 or IgG1k isotype control. IL-2 levels in the supernatants were measured after 18 h of incubation using the Human IL-2 ELISA Set™ (BD Biosciences, Cat. #555190).

Assessment of Primary CD4$^+$ T Cell Proliferation.

Primary CD4$^+$ T cells isolated and incubated with beads as mentioned above were then chased for 12 h with Bromodeoxyuridine (5-bromo-2-deoxyuridine, BrdU, BD Biosciences, Cat. #556028). Cells were then fixed and permeabilized in 100 µl of BD Cytofix™ (BD Biosciences, Cat #554555) containing 0.01% Tween and stained with anti-BrdU according to the manufacturer's instructions as well as with 2 µl of PE-conjugated anti-Ki67 (BD Biosciences, Cat #556027).

Sample Preparation for Phospho Western Blot.

After 18 hours of incubation with beads, Jurkat T cells attached to the beads were pelleted by quick centrifugation and the supernatant was discarded. An appropriate volume (between 120 to 240 µl per 10$^6$ cells) of lysis buffer (50 nm Tris-Cl, pH 7.5, 1 mM EDTA and EGTA, activated Na$_3$VO$_4$, 10 mM sodium B-glycerophosphate, 50 mM sodium fluoride, 5 mM sodium pyrophosphate, 1% NP40, 4% v/v of a stock solution prepared from Complete™ protease inhibitor cocktail tablets (Roche Diagnostics, Cat. #1-697-498, prepared according to manufacturer's instructions)) was added to the pellet, followed by vigorous agitation (by pipetting up and down several times). The lysis mixture was incubated on ice for 15 to 30 minutes with periodic agitation as described above. After this incubation, the mixture was sonicated briefly (1×4 sec.) at amplitude 20-25, and centrifuged in order to pellet beads and cell debris. The lysis supernatant was transferred to a fresh tube and stored at −80° C. until use. 30 μl of the lysis supernatant was mixed with 13 μl of 3× Laemmli loading buffer, boiled for 5 min., and loaded onto a polyacrylamide gel.

Electrophoresis was carried out at a constant voltage of 100 V. Cellular proteins were transferred electrophoretically to a polyvinylidene difluoride (PVDF) membrane. The transfer buffer contained 96 mM glycine, 10 mM Tris and 10% methanol. The transfer was carried out for 1 h at constant amperage of 80 mA/gel. Hydrophobic or nonspecific sites were blocked overnight at 4° C. with 5% powdered skim milk in Tris-buffered saline (50 mM Tris and 150 mM NaCl) containing 0.1% Tween™ 20 (TBS-T). Membranes were washed four times for 15 min in TBS-T. The blots were probed with the primary antibody: anti-phospho-SLP76 (BD Biosciences, cat #558388), anti-phospho-Fyn (BD Biosciences, cat #612688), anti-Lck505 (cat #sc-433), anti-CSK (cat #sc-286), anti-phospho-NFATc1 (cat #sc-32975) (Santa Cruz Biotechnology, Santa Cruz, Calif.), anti-phospho-SHP-2 tyr524 (cat #3751), anti-phospho-SHP-2 tyr580 (cat #3703), anti-SHP-2 (cat #3752), anti-phospho-Lck505 (cat #2751), anti-phospho-c-cbl774 (cat #3555), anti-phospho-ERK (cat #9101), anti-phospho-FOXO3a (cat #9466), anti-phospho-Ikbα (cat #9246), anti-phospho-IKK α/b (cat #2694), anti-phospho-NFkb p65 (cat #3037), anti-phospho-MEK (cat #9121) (Cell Signaling Technology, Beverly, Mass.), anti-actin (Sigma) in TBS-T, 1% bovine serum albumin (BSA) for 1 h at room temperature. Membranes were washed four times for 15 min and incubated for 1 h at room temperature with peroxidase-conjugated secondary antibody (1:1000) in TBS-T containing 5% milk powder. Secondary antibodies consisted of horseradish peroxidase (HRP)-conjugated goat anti-mouse (Pierce) and anti-rabbit (Jackson Immunoresearch). PVDF membranes were washed four times for 15 min and antibodies were detected using the ECL Plus™ chemiluminescence kit (PerkinElmer, Boston, Mass.). For verification of equivalence in protein loading, the blot was probed with the anti-actin antibody. Protein expression was quantified using a scanning laser densitometer, relative to β-actin.

Gene Expression Profiling Following PD-1 Engagement.

Jurkat T cells expressing PD-1 were incubated with beads coated with anti-CD3+ anti-CD28, and anti-PD-1 or an isotype control. 1×10$^6$ cells were harvested at time points 30 min, 3 hrs, 6 hrs, and 18 hrs, lysed for RNA extraction using Qiagen RNeasy™ kit (Cat #74104) according to the manufacturer's instructions. DNA was then hybridized on Illumina™ chips (according to the Ambion/Illumina kit, hybridization was performed in a 55° C. oven for 16-18 hours), scanned and analyzed. Quantification was done using Illumina BeadStation™ 500GX scanner and Illumina BeadStudio™ 3 Software. Illumina gene averaged data was exported from BeadStudio™ as raw data and was screened for quality (visual inspection of the chip image, analysis of the Illumina controls, diagnostic plots). Outliers were removed before subsequent analysis. The data was normalized using quantile method. Genes having intensities below background across all samples were filtered out and values below background were surrogate replaced. The data was log 2 transformed before its analysis in R statistical package "Linear models for microarray analysis" (LIMMA) where a fold change greater or equal to 1.5, or less or equal to −1.5 and a moderated p-value less or equal to 0.05 was considered significant.

Example 2

Development of an In Vitro System to Study PD-1 Signalling

The model comprises magnetic beads that are coated with anti-CD3, anti-CD28 and anti-PD-1 antibodies. As a negative control for PD-1 engagement, another set of beads coated with anti-CD3, anti-CD28 and isotype control antibodies. The amount of antibodies coated on the beads has been optimized to achieve optimal PD-1 mediated function, as measured by inhibition of IL-2 secretion. A diagram showing the bead system is found in FIG. 1. As shown in FIG. 1, beads coated with anti-CD3/CD28/PD-1 or anti-CD3/CD28/isotype were incubated with cells expressing PD-1. The cells used in the studies described herein are 1) Jurkat T cells stably expressing human PD-1, or primary CD4$^+$ T cells constitutively expressing PD-1 (obtained from HIV subjects) or after induction (healthy subjects). Cells and beads were incubated at 37° C. for various time periods: 18 hours for assessment of IL-2 production and proliferation); 9 minutes for Western Blotting; or 30 min, 3 hrs, 6 hrs, and 18 hrs for gene expression profiling.

Example 3

Effects of PD-1 Triggering on T Cell Function

Figure 2:
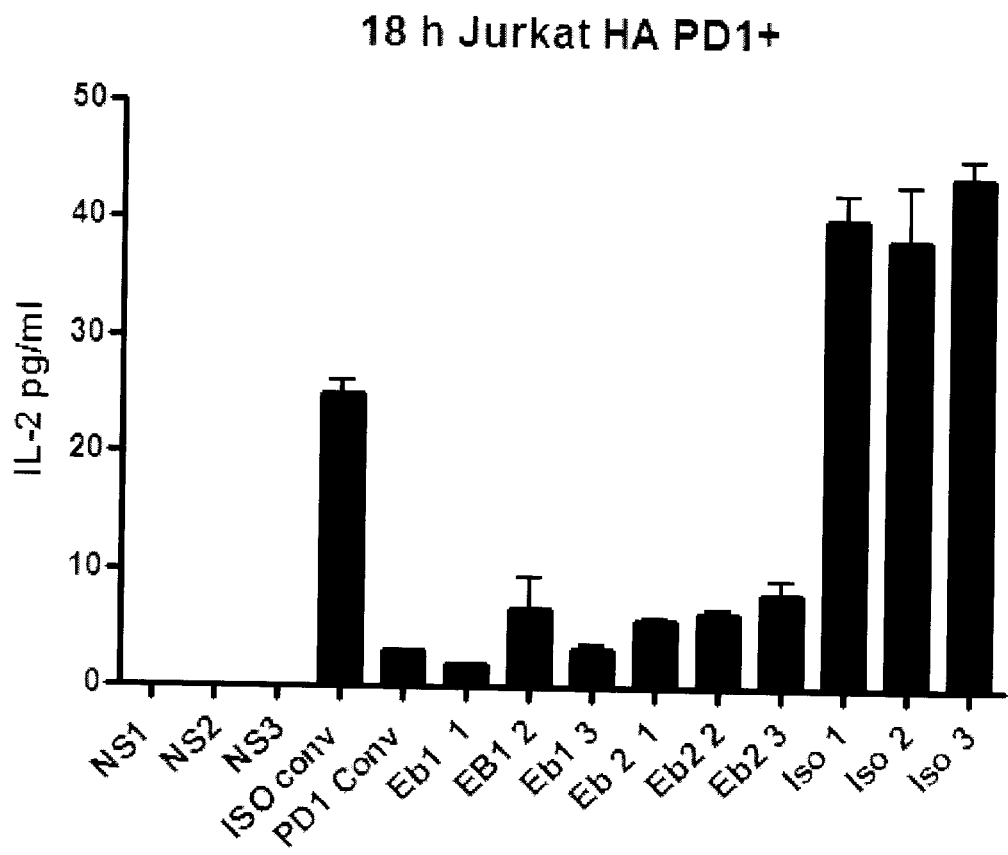
FIG. 2 shows the secretion of interleukin-2 (IL-2) by Jurkat T cells transfected with PD-1 under various conditions. Jurkat cells were incubated for 18 hours with beads either uncoated or coated with anti-CD3 and/or anti-CD28 and/or anti-PD-1 monoclonal antibodies. The concentration of IL-2 in the supernatant after the incubation was measured by ELISA. NS=unstimulated; "Eb1"=anti-PD1, clone J105 (cat #14-2799); "Eb2"=anti-PD1, clone J116 (cat #16-9989); "PD1 conventional"=antibody clone EH12 (Velu et al., 2007. *J. Virol.* 81: 5819-5828); Results for three independent experiments (numbered 1, 2 and 3) are presented.

The effect of PD-1 engagement on Jurkat T cells was tested by measuring 1) the secretion of IL-2, 2) the proliferation and 3) the levels of TCR signalling mediators, in T cells incubated in the presence of CD3/CD28/PD-1 coated beads. FIG. 2 shows that anti-PD-1 coated beads significantly inhibited the secretion of IL-2 by activated, PD-1$^+$ Jurkat T cells.

Figure 3:
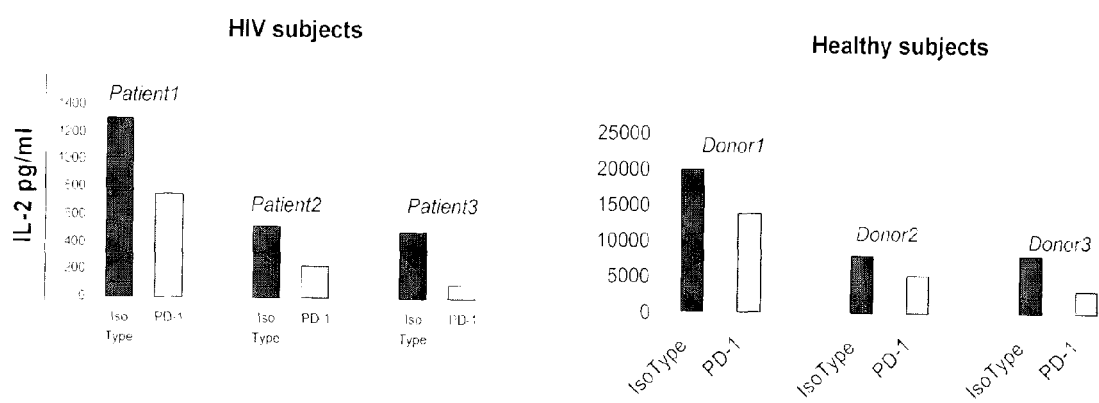
FIG. 3 shows the secretion of IL-2 by primary CD4$^+$ T cells from HIV-infected (left graph) or healthy (right graph) subjects under various conditions. Cells were incubated for 18 hours with beads coated with antibodies against CD3 and CD28, and either an anti-PD-1 antibody or an isotype control. The concentration of IL-2 in the supernatant after the incubation was measured by ELISA.

The effect of beads coated with PD-1 antibodies on IL-2 secretion was next tested in primary CD4$^+$ T cells. FIG. 3 shows that the secretion of IL-2 by primary CD4$^+$ T cells isolated from healthy subjects and HIV-infected subjects is also inhibited by the engagement of PD-1 during CD3/CD28-mediated T cell stimulation.

Figure 4:
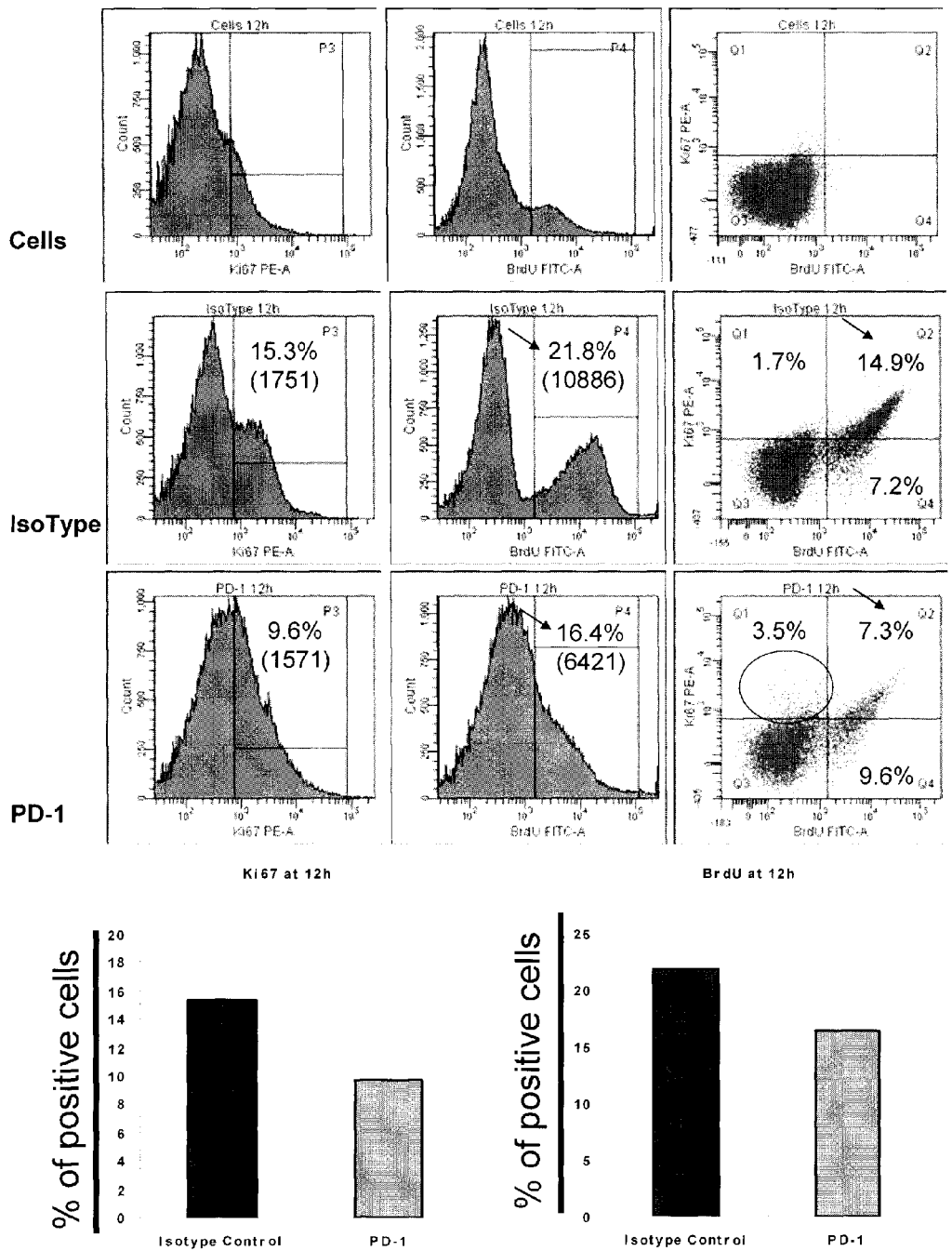
FIG. 4 shows the proliferation of primary CD4$^+$ T cells under various conditions. Cells were incubated for 18 hours with beads coated with antibodies against CD3 and CD28, and either an anti-PD-1 antibody or an isotype control, then chased for 12 h with Bromodeoxyuridine (5-bromo-2-deoxyuridine, BrdU). Cells were then fixed, permeabilized and stained with anti-BrdU and/or anti-Ki67 antibodies.

As shown in FIG. 4, PD-1 triggering also leads to an inhibition of the proliferation of primary CD4$^+$ T cells, as demonstrated by the decrease in BrdU incorporation and Ki67 staining in T cells stimulated in presence of PD-1-coated beads, as compared to cells stimulated in presence of isotype-coated beads.

Figure 5:
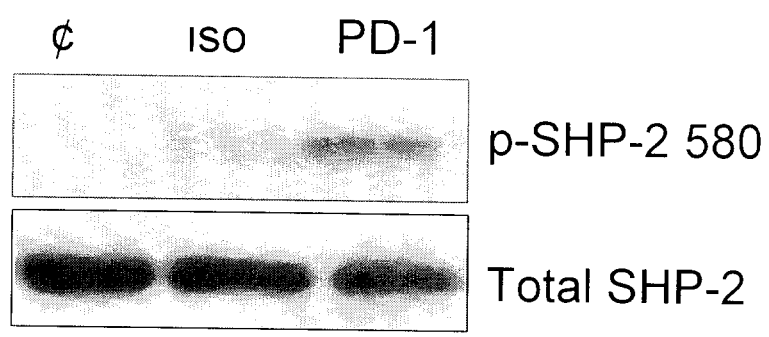
FIG. 5 shows the phosphorylation of SHP-2 in Jurkat T cells transfected with PD-1 under various conditions. Cells were incubated for 9 minutes with beads either uncoated (¢) or coated with antibodies against CD3 and CD28, and either an anti-PD-1 antibody (PD-1) or an isotype control (iso). The amount of phosphorylated SHP-2 was determined by Western blot, and the amount of total SHP-2 was determined as a control for equal loading. Data are representative of ten independent experiments.
Figure 6:
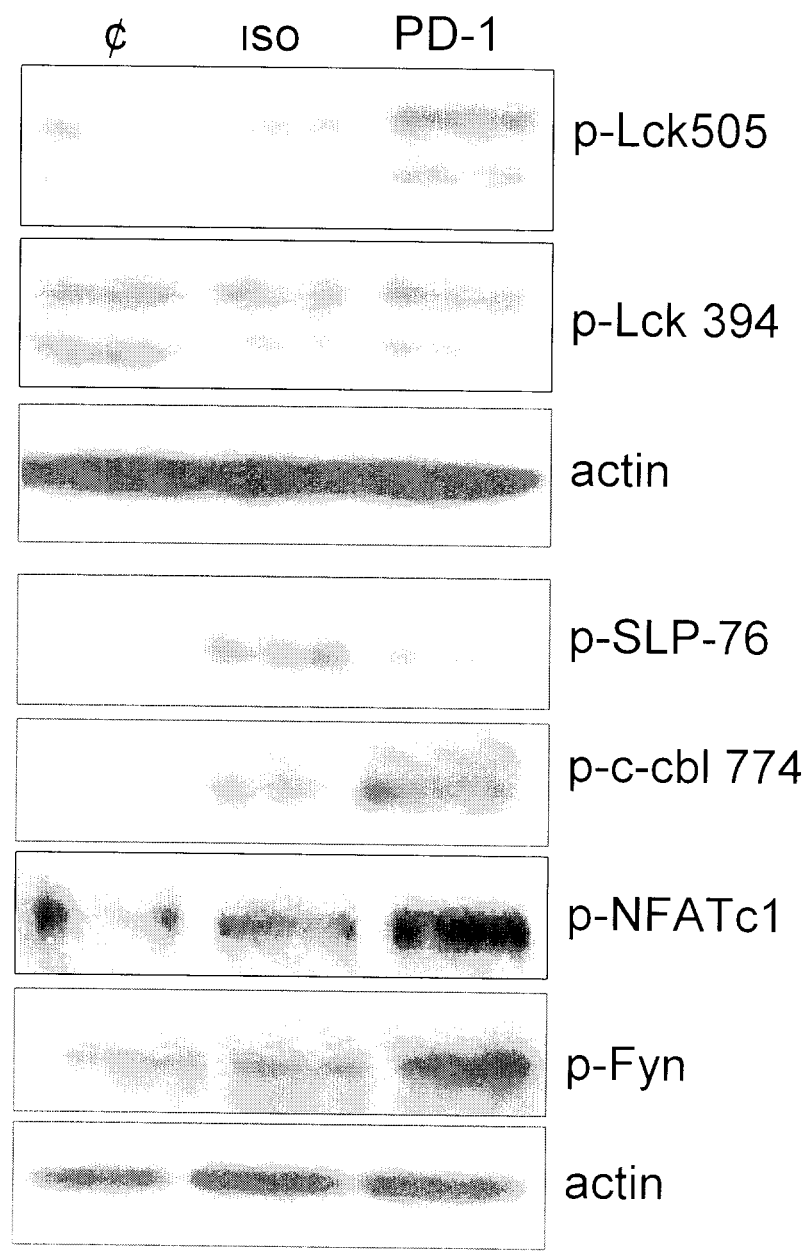
FIG. 6 shows the effects of PD-1 engagement on various T cell receptor (TCR) signalling components in Jurkat T cells transfected with PD-1. Cells were incubated for 9 minutes with beads either uncoated (¢) or coated with antibodies against CD3 and CD28, and either an anti-PD-1 antibody (PD-1) or an isotype control (iso). The amount of several phosphorylated proteins involved in TCR signalling (indicated on right) was determined by Western blot; Data are representative of four independent experiments.

The effect of PD-1 engagement on the level/activity of proteins involved in TCR signalling following CD3/CD28-mediated activation was next investigated. As shown in FIG. 5, the level of phosphorylated SHP-2 (phosphorylation of a tyrosine at position 580) is higher in T cells stimulated in the presence of anti-PD-1, as compared to those stimulated in the presence of the isotype control. Protein tyrosine phosphatase SHP-2 is known to down-regulate antigen receptor signalling and T cell activation (Hoff et al., 2007. *Eur. J. Immunol.* 37: 1072-86), and its phosphorylation at position 580 correlates with increased activity (Lu et al., 2001. *Mol Cell* 8: 759-769). PD-1 triggering further leads to an increase in the level of p56$^{lck}$ phosphorylated at Tyrosine 505 (p-Lck505, FIG. 6). The protein tyrosine kinase p56$^{lck}$ is involved in TCR signalling and phosphorylation at Tyr505 is associated with reduced activity as compared to the unphosphorylated form. PD-1 engagement is also associated with reduced activity of SLP-76, as demonstrated by the decreased level of phosphorylated SLP-76 (p-SLP-76, FIG. 6) in T cells stimulated in the presence of PD-1.

Example 4

Gene Expression Signature of PD-1 Triggering During T Cell Activation

To identify the gene expression profile associated with PD-1 engagement during T cell activation, the gene expression signature of Jurkat T cells incubated with beads coated with anti-CD3+anti-CD28+anti-PD-1 was compared to the signature of Jurkat T cells incubated with beads coated with anti-CD3+anti-CD28+isotype control. The gene expression signatures were compared at the following time points: after 30 min, 3 hrs, 6 hrs, and 18 hrs of incubation with the antibody-coated beads. Table II shows the list of genes whose expression significantly differs (at least 1.5-fold) in T cells activated in presence of anti-PD-1 as compared to those incubated with the isotype control. The nucleotide and amino acid sequences of the nucleic acids and polypeptides disclosed in Table II (SEQ ID NOs: 1 to 492) are provided in the sequence listing. Of note, we found changes in expression levels of genes who are members of the TNFSF and TNFRSF (CD27, TNFSF14, CD70 (also known as CD27L) and ICOS), cytokines and genes of the KLF (KLF2, KLF6) family. Tables III to VI shows the list of genes whose expression significantly differs in T cells activated in presence of anti-PD-1 as compared to those incubated with the isotype control at 30 min (Table III), 3 hours (Table IV), 6 hours (Table V) and 18 hours post-activation (Table VI). Genes in bold in Table III to VI are the genes whose expression is higher in T cells exposed to anti-PD-1 as compared to cells exposed to the isotype control. Table VII provides the nucleotide sequence of the oligonucleotides used for the detection of the genes.

TABLE II

Genes having different expression profiles in T cells exposed to anti-PD-1 vs. isotype control at one or more time points

| Gene name | RefSeq (nucleic acid) | RefSeq (protein) | SEQ ID NO: Nucleic acid/protein |
|---|---|---|---|
| CD55 | NM_000574.2 | NP_000565.1 | SEQ ID NO: 1/2 |
| NFKB2 | NM_001077493.1 | NP_001070961.1 | SEQ ID NO: 3/4 |
|  | NM_001077494.1 | NP_001070962.1 | SEQ ID NO: 5/6 |
|  | NM_002502.3 | NP_002493.3 | SEQ ID NO: 7/8 |
| FAM65A | NM_024519.2 | NP_078795.2 | SEQ ID NO: 9/10 |
| DIP | NM_015124.2 | NP_055939.1 | SEQ ID NO: 11/12 |
| STS-1 | NM_032873.3 | NP_116262.2 | SEQ ID NO: 13/14 |
| TPST2 | NM_001008566.1 | NP_001008566.1 | SEQ ID NO: 15/16 |
|  | NM_003595.3 | NP_003586.3 | SEQ ID NO: 17/18 |
| E4F1 | NM_004424.3 | NP_004415.2 | SEQ ID NO: 19/20 |
| CST7 | NM_003650.2 | NP_003641.2 | SEQ ID NO: 21/22 |
| GNG4 | NM_001098721.1 | NP_001092191.1 | SEQ ID NO: 23/24 |
|  | NM_001098722.1 | NP_001092192.1 | SEQ ID NO: 25/26 |
|  | NM_004485.3 | NP_004476.1 | SEQ ID NO: 27/28 |
| CD70 | NM_001252.3 | NP_001243.1 | SEQ ID NO: 29/30 |
| BACH2 | NM_021813.1 | NP_068585.1 | SEQ ID NO: 31/32 |
| REL | NM_002908.2 | NP_002899.1 | SEQ ID NO: 33/34 |
| PAM | NM_000919.2 | NP_000910.2 | SEQ ID NO: 35/36 |
|  | NM_138766.1 | NP_620121.1 | SEQ ID NO: 37/38 |
|  | NM_138821.1 | NP_620176.1 | SEQ ID NO: 39/40 |
|  | NM_138822.1 | NP_620177.1 | SEQ ID NO: 41/42 |
| KIAA0831 | NM_014924.3 | NP_055739.2 | SEQ ID NO: 43/44 |
| LOC197322 | NM_174917.1 | NP_777577.1 | SEQ ID NO: 45/46 |
| IL2RA | NM_000417.1 | NP_000408.1 | SEQ ID NO: 47/48 |
| IL13 | NM_002188.2 | NP_002179.2 | SEQ ID NO: 49/50 |
| LPIN1 | NM_145693.1 | NP_663731.1 | SEQ ID NO: 51/52 |
| CBFA2T3 | NM_005187.4 | NP_005178.4 | SEQ ID NO: 53/54 |
|  | NM_175931.1 | NP_787127.1 | SEQ ID NO: 55/56 |
| KRT1 | NM_006121.3 | NP_006112.3 | SEQ ID NO: 57/58 |
| MT1A | NM_005946.2 | NP_005937.2 | SEQ ID NO: 59/60 |
| ANKRD5 | NM_022096.4 | NP_071379.3 | SEQ ID NO: 61/62 |
|  | NM_198798.1 | NP_942093.1 | SEQ ID NO: 6364 |
| NQO1 | NM_000903.2 | NP_000894.1 | SEQ ID NO: 65/66 |
|  | NM_001025433.1 | NP_001020604.1 | SEQ ID NO: 67/68 |
|  | NM_001025434.1 | NP_001020605.1 | SEQ ID NO: 69/70 |
| KLF6 | NM_001008490.1 | NP_001008490.1 | SEQ ID NO: 71/72 |
|  | NM_001300.4 | NP_001291.3 | SEQ ID NO: 73/74 |
| CENPE | NM_001813.2 | NP_001804.2 | SEQ ID NO: 75/76 |
| SMOX | NM_175839.1 | NP_787033.1 | SEQ ID NO: 77/78 |
|  | NM_175840.1 | NP_787034.1 | SEQ ID NO: 79/80 |
|  | NM_175841.1 | NP_787035.1 | SEQ ID NO: 81/82 |
|  | NM_175842.1 | NP_787036.1 | SEQ ID NO: 83/84 |
| FBXO34 | NM_017943.2 | NP_060413.2 | SEQ ID NO: 85/86 |
| LZTS1 | NM_021020.1 | NP_066300.1 | SEQ ID NO: 87/88 |
| LAMP3 | NM_014398.2 | NP_055213.2 | SEQ ID NO: 89/90 |
| SPEN | NM_015001.2 | NP_055816.2 | SEQ ID NO: 91/92 |
| SH2B3 | NM_005475.1 | NP_005466.1 | SEQ ID NO: 93/94 |
| TNF | NM_000594.2 | NP_000585.2 | SEQ ID NO: 95/96 |
| BAT2D1 | NM_015172.3 | NP_055987.2 | SEQ ID NO: 97/98 |
| ZYX | NM_001010972.1 | NP_001010972.1 | SEQ ID NO: 99/100 |
|  | NM_003461.4 | NP_003452.1 | SEQ ID NO: 101/102 |
| SPTBN1 | NM_003128.2 | NP_003119.2 | SEQ ID NO: 103/104 |
|  | NM_178313.2 | NP_842565.2 | SEQ ID NO: 105/106 |

TABLE II-continued

Genes having different expression profiles in T cells exposed to anti-PD-1 vs. isotype control at one or more time points

| Gene name | RefSeq (nucleic acid) | RefSeq (protein) | SEQ ID NO: Nucleic acid/protein |
|---|---|---|---|
| ATP1B1 | NM_001001787.1 | NP_001001787.1 | SEQ ID NO: 107/108 |
|  | NM_001677.3 | NP_001668.1 | SEQ ID NO: 109/110 |
| SLA | NM_001045556.1 | NP_001039021.1 | SEQ ID NO: 111/112 |
|  | NM_001045557.1 | NP_001039022.1 | SEQ ID NO: 113/114 |
|  | NM_006748.2 | NP_006739.1 | SEQ ID NO: 115/116 |
| PLAU | NM_002658.2 | NP_002649.1 | SEQ ID NO: 117/118 |
| SOCS1 | NM_003745.1 | NP_003736.1 | SEQ ID NO: 119/120 |
| OSGIN1 | NM_013370.3 | NP_037502.3 | SEQ ID NO: 121/122 |
|  | NM_182980.2 | NP_892025.1 | SEQ ID NO: 123/124 |
|  | NM_182981.2 | NP_892026.1 | SEQ ID NO: 125/126 |
| BRD2 | NM_005104.2 | NP_005095.1 | SEQ ID NO: 127/128 |
| VGF | NM_003378.2 | NP_003369.2 | SEQ ID NO: 129/130 |
| PTPN6 | NM_002831.4 | NP_002822.2 | SEQ ID NO: 131/132 |
|  | NM_080548.3 | NP_536858.1 | SEQ ID NO: 133/134 |
| TNFSF14 | NM_003807.2 | NP_003798.2 | SEQ ID NO: 135/136 |
|  | NM_172014.1 | NP_742011.1 | SEQ ID NO: 137/138 |
| IL2 | NM_000586.3 | NP_000577.2 | SEQ ID NO: 139/140 |
| CD97 | NM_001025160.1 | NP_001020331.1 | SEQ ID NO: 141/142 |
|  | NM_001784.3 | NP_001775.2 | SEQ ID NO: 143/144 |
|  | NM_078481.2 | NP_510966.1 | SEQ ID NO: 145/146 |
| RPL28 | NM_000991.3 | NP_000982.2 | SEQ ID NO: 147/148 |
| CSF2 | NM_000758.2 | NP_000749.2 | SEQ ID NO: 149/150 |
| CCAR1 | NM_018237.2 | NP_060707.2 | SEQ ID NO: 151/152 |
| RPL7L1 | NM_198486.2 | NP_940888.2 | SEQ ID NO: 153/154 |
| CD83 | NM_001040280.1 | NP_001035370.1 | SEQ ID NO: 155/156 |
|  | NM_004233.3 | NP_004224.1 | SEQ ID NO: 157/158 |
| MIDN | NM_177401.4 | NP_796375.3 | SEQ ID NO: 159/160 |
| BCL2L1 | NM_001191.2 | NP_001182.1 | SEQ ID NO: 161/162 |
|  | NM_138578.1 | NP_612815.1 | SEQ ID NO: 163/164 |
| LUZP1 | NM_033631.2 | NP_361013.2 | SEQ ID NO: 165/166 |
| VHL | NM_000551.2 | NP_000542.1 | SEQ ID NO: 167/168 |
|  | NM_198156.1 | NP_937799.1 | SEQ ID NO: 169/170 |
| CCL20 | NM_004591.1 | NP_004582.1 | SEQ ID NO: 171/172 |
| PCNT | NM_006031.4 | NP_006022.3 | SEQ ID NO: 173/174 |
| SPRY1 | NM_005841.1 | NP_005832.1 | SEQ ID NO: 175/176 |
|  | NM_199327.1 | NP_955359.1 | SEQ ID NO: 177/178 |
| RUNX3 | NM_001031680.2 | NP_001026850.1 | SEQ ID NO: 179/180 |
|  | NM_004350.2 | NP_004341.1 | SEQ ID NO: 181/182 |
| BCL2A1 | NM_004049.2 | NP_004040.1 | SEQ ID NO: 183/184 |
| MBP | NM_001025094.1 | NP_001020265.1 | SEQ ID NO: 185/186 |
|  | NM_001025098.1 | NP_001020269.1 | SEQ ID NO: 187/188 |
|  | NM_001025081.1 | NP_001020252.1 | SEQ ID NO: 189/190 |
|  | NM_001025090.1 | NP_001020261.1 | SEQ ID NO: 191/192 |
|  | NM_001025092.1 | NP_001020263.1 | SEQ ID NO: 193/194 |
|  | NM_001025100.1 | NP_001020271.1 | SEQ ID NO: 195/196 |
|  | NM_001025101.1 | NP_001020272.1 | SEQ ID NO: 197/198 |
|  | NM_002385.2 | NP_002376.1 | SEQ ID NO: 199/200 |
| RHOU | NM_021205.4 | NP_067028.1 | SEQ ID NO: 201/202 |
| RDH10 | NM_172037.2 | NP_742034.1 | SEQ ID NO: 203/204 |
| HTR2B | NM_000867.3 | NP_000858.2 | SEQ ID NO: 205/206 |
| DDEF1 | NM_018482.2 | NP_060952.2 | SEQ ID NO: 207/208 |
| GZMB | NM_004131.3 | NP_004122.2 | SEQ ID NO: 209/210 |
| TJAP1 | NM_080604.1 | NP_542171.1 | SEQ ID NO: 211/212 |
| MACF1 | NM_012090.3 | NP_036222.3 | SEQ ID NO: 213/214 |
|  | NM_033044.2 | NP_149033.2 | SEQ ID NO: 215/216 |
| RCBTB2 | NM_001268.2 | NP_001259.1 | SEQ ID NO: 217/218 |
| RGS16 | NM_002928.2 | NP_002919.2 | SEQ ID NO: 219/220 |
| JMJD1C | NM_004241.2 | NP_004232.2 | SEQ ID NO: 221/222 |
|  | NM_032776.1 | NP_116165.1 | SEQ ID NO: 223/224 |
| LTB | NM_002341.1 | NP_002332.1 | SEQ ID NO: 225/226 |
|  | NM_009588.1 | NP_033666.1 | SEQ ID NO: 227/228 |
| MYH9 | NM_002473.3 | NP_002464.1 | SEQ ID NO: 229/230 |
| CLIP3 | NM_015526.1 | NP_056341.1 | SEQ ID NO: 231/232 |
| GBE1 | NM_000158.2 | NP_000149.2 | SEQ ID NO: 233/234 |
| CCDC64 | NM_207311.2 | NP_997194.2 | SEQ ID NO: 235/236 |
| PHEX | NM_000444.3 | NP_000435.3 | SEQ ID NO: 237/238 |
| SNX26 | NM_052948.2 | NP_443180.2 | SEQ ID NO: 239/240 |
| TAGAP | NM_054114.3 | NP_473455.2 | SEQ ID NO: 241/242 |
|  | NM_138810.2 | NP_620165.1 | SEQ ID NO: 243/244 |
|  | NM_152133.1 | NP_687034.1 | SEQ ID NO: 245/246 |
| FAM50A | NM_004699.1 | NP_004690.1 | SEQ ID NO: 247/248 |
| TRAF1 | NM_005658.3 | NP_005649.1 | SEQ ID NO: 249/250 |
| CDK5RAP2 | NM_001011649.1 | NP_001011649.1 | SEQ ID NO: 251/252 |
|  | NM_018249.4 | NP_060719.4 | SEQ ID NO: 253/254 |

TABLE II-continued

Genes having different expression profiles in T cells exposed to anti-PD-1 vs. isotype control at one or more time points

| Gene name | RefSeq (nucleic acid) | RefSeq (protein) | SEQ ID NO: Nucleic acid/protein |
|---|---|---|---|
| TAF1C | NM_005679.2 | NP_005670.2 | SEQ ID NO: 255/256 |
|  | NM_139353.1 | NP_647610.1 | SEQ ID NO: 257/258 |
| KIAA1754 | NM_033397.2 | NP_203755.1 | SEQ ID NO: 259/260 |
| LRRC8C | NM_032270.2 | NP_115646.2 | SEQ ID NO: 261/262 |
| SUPT6H | NM_003170.3 | NP_003161.2 | SEQ ID NO: 263/264 |
| IL23A | NM_016584.2 | NP_057668.1 | SEQ ID NO: 265/266 |
| SH2D2A | NM_003975.2 | NP_003966.1 | SEQ ID NO: 267/268 |
| IL21R | NM_021798.2 | NP_068570.1 | SEQ ID NO: 269/270 |
|  | NM_181078.1 | NP_851564.1 | SEQ ID NO: 271/272 |
|  | NM_181079.1 | NP_851565.1 | SEQ ID NO: 273/274 |
| ATP6V0A4 | NM_020632.2 | NP_065683.2 | SEQ ID NO: 275/276 |
|  | NM_130840.2 | NP_570855.2 | SEQ ID NO: 277/278 |
|  | NM_130841.2 | NP_570856.2 | SEQ ID NO: 279/280 |
| TNFRSF8 | NM_001243.3 | NP_001234.2 | SEQ ID NO: 281/282 |
|  | NM_152942.2 | NP_694421.1 | SEQ ID NO: 283/284 |
| MAPRE2 | NM_014268.1 | NP_055083.1 | SEQ ID NO: 285/286 |
| TMEM158 | NM_015444.2 | NP_056259.2 | SEQ ID NO: 287/288 |
| ITGA5 | NM_002205.2 | NP_002196.2 | SEQ ID NO: 289/290 |
| JAM3 | NM_032801.3 | NP_116190.2 | SEQ ID NO: 291/292 |
| BAZ1A | NM_013448.2 | NP_038476.2 | SEQ ID NO: 293/294 |
|  | NM_182648.1 | NP_872589.1 | SEQ ID NO: 295/296 |
| IL3 | NM_000588.3 | NP_000579.2 | SEQ ID NO: 297/298 |
| FOS | NM_005252.2 | NP_005243.1 | SEQ ID NO: 299/300 |
| HES4 | NM_021170.2 | NP_066993.1 | SEQ ID NO: 301/302 |
| TIMP1 | NM_003254.2 | NP_003245.1 | SEQ ID NO: 303/304 |
| TNS3 | NM_022748.10 | NP_073585.8 | SEQ ID NO: 305/306 |
| NFKBIA | NM_020529.1 | NP_065390.1 | SEQ ID NO: 307/308 |
| CGA | NM_000735.2 | NP_000726.1 | SEQ ID NO: 309/310 |
| TSC22D1 | NM_006022.2 | NP_006013.1 | SEQ ID NO: 311/312 |
|  | NM_183422.1 | NP_904358.1 | SEQ ID NO: 313/314 |
| EIF4G3 | NM_003760.3 | NP_003751.2 | SEQ ID NO: 315/316 |
| ATP6V1B2 | NM_001693.3 | NP_001684.2 | SEQ ID NO: 317/318 |
| DUSP1 | NM_004417.2 | NP_004408.1 | SEQ ID NO: 319/320 |
| SLC9A1 | NM_003047.2 | NP_003038.2 | SEQ ID NO: 321/322 |
| MEF2D | NM_005920.2 | NP_005911.1 | SEQ ID NO: 323/324 |
| SNAPC4 | NM_003086.2 | NP_003077.2 | SEQ ID NO: 325/326 |
| GPR171 | NM_013308.3 | NP_037440.3 | SEQ ID NO: 327/328 |
| CD27 | NM_001242.4 | NP_001233.1 | SEQ ID NO: 329/330 |
| ALDOC | NM_005165.2 | NP_005156.1 | SEQ ID NO: 331/332 |
| TNFRSF21 | NM_014452.3 | NP_055267.1 | SEQ ID NO: 333/334 |
| DPP9 | NM_139159.3 | NP_631898.2 | SEQ ID NO: 335/336 |
| SRRM2 | NM_016333.3 | NP_057417.3 | SEQ ID NO: 337/338 |
| METT11D1 | NM_001029992.1 | NP_001025163.1 | SEQ ID NO: 339/340 |
|  | NM_001029991.1 | NP_001025162.1 | SEQ ID NO: 341/342 |
|  | NM_022734.2 | NP_073571.1 | SEQ ID NO: 343/344 |
| CD69 | NM_001781.1 | NP_001772.1 | SEQ ID NO: 345/346 |
| IRX5 | NM_005853.5 | NP_005844.4 | SEQ ID NO: 347/348 |
| TBC1D10C | NM_198517.2 | NP_940919.1 | SEQ ID NO: 349/350 |
| PLAGL2 | NM_002657.2 | NP_002648.1 | SEQ ID NO: 351/352 |
| KLF2 | NM_016270.2 | NP_057354.1 | SEQ ID NO: 353/354 |
| PRR14 | NM_024031.2 | NP_076936.1 | SEQ ID NO: 355/356 |
| BIRC3 | NM_001165.3 | NP_001156.1 | SEQ ID NO: 357/358 |
|  | NM_182962.1 | NP_892007.1 | SEQ ID NO: 359/360 |
| FSCN1 | NM_003088.2 | NP_003079.1 | SEQ ID NO: 361/362 |
| IGFBP2 | NM_000597.2 | NP_000588.2 | SEQ ID NO: 363/364 |
| LTBP4 | NM_001042544.1 | NP_001036009.1 | SEQ ID NO: 365/366 |
|  | NM_001042545.1 | NP_001036010.1 | SEQ ID NO: 367/368 |
|  | NM_003573.2 | NP_003564.2 | SEQ ID NO: 369/370 |
| USP11 | NM_004651.3 | NP_004642.2 | SEQ ID NO: 371/372 |
| BHLHB2 | NM_003670.1 | NP_003661.1 | SEQ ID NO: 373/374 |
| ARC | NM_015193.3 | NP_056008.1 | SEQ ID NO: 375/376 |
| PPP1R15A | NM_014330.2 | NP_055145.2 | SEQ ID NO: 377/378 |
| AUTS2 | NM_015570.1 | NP_056385.1 | SEQ ID NO: 379/380 |
| RXRA | NM_002957.3 | NP_002948.1 | SEQ ID NO: 381/382 |
| MARVELD3 | NM_001017967.2 | NP_001017967.2 | SEQ ID NO: 383/384 |
|  | NM_052858.3 | NP_443090.2 | SEQ ID NO: 385/386 |
| ARG2 | NM_001172.3 | NP_001163.1 | SEQ ID NO: 387/388 |
| SETD2 | NM_014159.4 | NP_054878.3 | SEQ ID NO: 389/390 |
| CENPF | NM_016343.3 | NP_057427.3 | SEQ ID NO: 391/392 |
| ADORA2A | NM_000675.3 | NP_000666.2 | SEQ ID NO: 393/394 |
| FOSB | NM_006732.1 | NP_006723.1 | SEQ ID NO: 395/396 |
| EGR2 | NM_000399.2 | NP_000390.2 | SEQ ID NO: 397/398 |
| LAIR2 | NM_002288.3 | NP_002279.2 | SEQ ID NO: 399/400 |
|  | NM_021270.2 | NP_067154.1 | SEQ ID NO: 401/402 |

TABLE II-continued

Genes having different expression profiles in T cells exposed to anti-PD-1 vs. isotype control at one or more time points

| Gene name | RefSeq (nucleic acid) | RefSeq (protein) | SEQ ID NO: Nucleic acid/protein |
|---|---|---|---|
| CBX6 | NM_014292.3 | NP_055107.3 | SEQ ID NO: 403/404 |
| PHACTR4 | NM_001048183.1 | NP_001041648.1 | SEQ ID NO: 405/406 |
|  | NM_023923.3 | NP_076412.3 | SEQ ID NO: 407/408 |
| CCL4L1 | NM_001001435.2 | NP_001001435.1 | SEQ ID NO: 409/410 |
| ULK1 | NM_003565.1 | NP_003556.1 | SEQ ID NO: 411/412 |
| PTPN22 | NM_012411.2 | NP_036543.2 | SEQ ID NO: 413/414 |
|  | NM_015967.3 | NP_057051.2 | SEQ ID NO: 415/416 |
| GNL3L | NM_019067.4 | NP_061940.1 | SEQ ID NO: 417/418 |
| ZCCHC6 | NM_024617.2 | NP_078893.2 | SEQ ID NO: 419/420 |
| PRKCH | NM_006255.3 | NP_006246.2 | SEQ ID NO: 421/422 |
| MFSD2 | NM_032793.2 | NP_116182.2 | SEQ ID NO: 423/424 |
| TMEM187 | NM_003492.2 | NP_003483.1 | SEQ ID NO: 425/426 |
| C6orf190 | NM_001010923.1 | NP_001010923.1 | SEQ ID NO: 427/428 |
| ITPR3 | NM_002224.2 | NP_002215.2 | SEQ ID NO: 429/430 |
| ADM | NM_001124.1 | NP_001115.1 | SEQ ID NO: 431/432 |
| MT2A | NM_005953.2 | NP_005944.1 | SEQ ID NO: 433/434 |
| EOMES | NM_005442.2 | NP_005433.2 | SEQ ID NO: 435/436 |
| POU2AF1 | NM_006235.1 | NP_006226.1 | SEQ ID NO: 437/438 |
| NFATC1 | NM_006162.3 | NP_006153.2 | SEQ ID NO: 439/440 |
|  | NM_172387.1 | NP_765975.1 | SEQ ID NO: 441/442 |
|  | NM_172388.1 | NP_765976.1 | SEQ ID NO: 443/444 |
|  | NM_172389.1 | NP_765977.1 | SEQ ID NO: 445/446 |
|  | NM_172390.1 | NP_765978.1 | SEQ ID NO: 447/448 |
| C1orf165 | NM_024603.1 | NP_078879.1 | SEQ ID NO: 449/450 |
| ZFP36 | NM_003407.2 | NP_003398.1 | SEQ ID NO: 451/452 |
| BCL9 | NM_004326.2 | NP_004317.2 | SEQ ID NO: 453/454 |
| NOTCH1 | NM_017617.3 | NP_060087.3 | SEQ ID NO: 455/456 |
| POLE | NM_006231.2 | NP_006222.2 | SEQ ID NO: 457/458 |
| LY96 | NM_015364.2 | NP_056179.1 | SEQ ID NO: 459/460 |
| CREBBP | NM_001079846.1 | NP_001073315.1 | SEQ ID NO: 461/462 |
|  | NM_004380.2 | NP_004371.2 | SEQ ID NO: 463/464 |
| EGR4 | NM_001965.2 | NP_001956.2 | SEQ ID NO: 465/466 |
| ACVR1 | NM_001105.2 | NP_001096.1 | SEQ ID NO: 467/468 |
| PFKFB4 | NM_004567.2 | NP_004558.1 | SEQ ID NO: 469/470 |
| NR4A2 | NM_006186.2 | NP_006177.1 | SEQ ID NO: 471/472 |
|  | NM_173171.1 | NP_775263.1 | SEQ ID NO: 473/474 |
|  | NM_173172.1 | NP_775264.1 | SEQ ID NO: 475/476 |
|  | NM_173173.1 | NP_775265.1 | SEQ ID NO: 477/478 |
| MYC | NM_002467.3 | NP_002458.2 | SEQ ID NO: 479/480 |
| CCL1 | NM_002981.1 | NP_002972.1 | SEQ ID NO: 481/482 |
| CXCR3 | NM_001504.1 | NP_001495.1 | SEQ ID NO: 483/484 |
| ICOS | NM_012092.2 | NP_036224.1 | SEQ ID NO: 485/486 |
| MAG1 | NM_032717.3 | NP_116106.2 | SEQ ID NO: 487/488 |
| FXYD5 | NM_014164.4 | NP_054883.3 | SEQ ID NO: 489/490 |
|  | NM_144779.1 | NP_659003.1 | SEQ ID NO: 491/492 |

TABLE III

Genes having different expression profiles in T cells exposed to anti-PD-1-vs. isotype control at 30 minutes post-activation
Gene name

| | | |
|---|---|---|
| FAM65A | MACF1 | PPP1R15A |
| E4F1 | MYH9 | AUTS2 |
| CBFA2T3 | CLIP3 | SETD2 |
| CENPE | SNX26 | CENPF |
| SPEN | CDK5RAP2 | FOSB |
| TNF | BAZ1A | EGR2 |
| BAT2D1 | FOS | PHACTR4 |
| SPTBN1 | EIF4G3 | ULK1 |
| BRD2 | DUSP1 | GNL3L |
| CCAR1 | SLC9A1 | ZCCHC6 |
| RPL7L1 | MEF2D | ITPR3 |
| MIDN | SNAPC4 | ZFP36 |
| VHL | SRRM2 | NOTCH1 |
| PCNT | KLF2 | POLE |
| RUNX3 | PRR14 | EGR4 |
| TJAP1 | BHLHB2 | |

TABLE IV

Genes having different expression profiles in T cells exposed to anti-PD-1-vs. isotype control at 3 hours post-activation
Gene name

| | | |
|---|---|---|
| E4F1 | GZMB | PLAGL2 |
| CBFA2T3 | TJAP1 | KLF2 |
| MT1A | MACF1 | PRR14 |
| ANKRD5 | JMJD1C | FSCN1 |
| KLF6 | SPRY1 | LTBP4 |
| SPEN | MYH9 | USP11 |
| TNF | CLIP3 | BHLHB2 |
| BAT2D1 | SNX26 | ARC |
| ZYX | TAGAP | PPP1R15A |
| SPTBN1 | FAM50A | AUTS2 |
| SLA | CDK5RAP2 | MARVELD3 |
| SOCS1 | TAF1C | SETD2 |
| OSGIN1 | KIAA1754 | CENPF |
| BRD2 | SUPT6H | CBX6 |
| VGF | SH2D2A | ULK1 |
| TNFSF14 | ATP6V0A4 | GNL3L |
| RPL28 | TNFRSF8 | ZCCHC6 |
| CSF2 | ITGA5 | ITPR3 |
| CCAR1 | IL3 | MT2A |

TABLE IV-continued

Genes having different expression profiles in T cells exposed to anti-PD-1-vs. isotype control at 3 hours post-activation
Gene name

| | | |
|---|---|---|
| RPL7L1 | TIMP1 | NFATC1 |
| MIDN | SLC9A1 | ZFP36 |
| LUZP1 | MEF2D | BCL9 |
| VHL | SNAPC4 | NOTCH1 |
| PCNT | DPP9 | POLE |
| SPRY1 | SRRM2 | CREBBP |
| RUNX3 | CD69 | ACVR1 |
| RDH10 | IRX5 | ICOS |
| DDEF1 | KLF6 | MAG1 |

TABLE V

Genes having different expression profiles in T cells exposed to anti-PD-1-vs. isotype control at 6 hours post-activation
Gene name

| | | |
|---|---|---|
| CD55 | SPRY1 | GPR171 |
| DIP | RUNX3 | CD27 |
| STS-1 | MBP | TNFRSF21 |
| CD70 | RDH10 | TBC1D10C |
| BACH2 | SPRY1 | KLF6 |
| REL | LTB | LTBP4 |
| KIAA0831 | MYH9 | MARVELD3 |
| CBFA2T3 | CCDC64 | ADORA2A |
| KLF6 | TAGAP | CCL4L1 |
| SMOX | TRAF1 | PTPN22 |
| FBXO34 | LRRC8C | PRKCH |
| LZTS1 | IL23A | BIRC3 |
| LAMP3 | SH2D2A | C6orf190 |
| SPEN | IL21R | ADM |
| SH2B3 | MAPRE2 | EOMES |
| ATP1B1 | TMEM158 | POU2AF1 |
| SLA | IL3 | NFATC1 |
| PLAU | FOS | LY96 |
| SOCS1 | TNS3 | ACVR1 |
| BRD2 | NFKBIA | MYC |
| PTPN6 | TSC22D1 | CCL1 |
| TNFSF14 | ATP1B1 | CXCR3 |
| CD97 | ATP6V1B2 | MAG1 |

TABLE V-continued

Genes having different expression profiles in T cells exposed to anti-PD-1-vs. isotype control at 6 hours post-activation
Gene name

| | | |
|---|---|---|
| CSF2 | DUSP1 | FXYD5 |
| CD83 | SLC9A1 | |

TABLE VI

Genes having different expression profiles in T cells exposed to anti-PD-1-vs. isotype control at 18 hours post-activation
Gene name

| | | |
|---|---|---|
| CD55 | RHOU | GPR171 |
| NFKB2 | RDH10 | CD27 |
| TPST2 | HTR2B | ALDOC |
| CST7 | GZMB | METT11D1 |
| GNG4 | RCBTB2 | CD69 |
| CD70 | RGS16 | PLAGL2 |
| REL | SPRY1 | KLF2 |
| PAM | LTB | BIRC3 |
| KIAA0831 | GBE1 | IGFBP2 |
| LOC197322 | CCDC64 | RXRA |
| IL2RA | PHEX | ARG2 |
| IL13 | TAGAP | CENPF |
| CBFA2T3 | TRAF1 | ADORA2A |
| KRT1 | CDK5RAP2 | LAIR2 |
| MT1A | LRRC8C | PTPN22 |
| NQO1 | IL23A | GNL3L |
| FBXO34 | SH2D2A | MFSD2 |
| LAMP3 | IL21R | BIRC3 |
| TNFSF14 | ATP6V0A4 | TMEM187 |
| IL2 | ITGA5 | C6orf190 |
| CD97 | JAM3 | ADM |
| CSF2 | IL3 | POU2AF1 |
| CD83 | HES4 | C1orf165 |
| BCL2L1 | TNS3 | PFKFB4 |
| CCL20 | NFKBIA | NR4A2 |
| SPRY1 | CGA | CCL1 |
| BCL2A1 | ATP6V1B2 | ICOS |
| MBP | | |

TABLE VII

Oligonucleotides/probes used for gene expression profiling.

| Gene name | Probe sequence | SEQ ID No: |
|---|---|---|
| CD55 | GGTAAAACATGCTGGTGAACCAGGGGTGTTGATGGTGATAAGGGAGGAAT | 493 |
| NFKB2 | AGCACAGAGGTGAAGGAAGACAGTGCGTACGGGAGCCAGTCAGTGGAGCA | 494 |
| FAM65A | GGCTTGGCCACCCTGCCGCTGCCCAGCCACATCCCTTGGTTTTGTATTTT | 495 |
| DIP | ATCGGCACGGGCTCTGGGCTCCCCGTGGAGAGAAGCTGTAGTTTTTACCA | 496 |
| STS-1 | TCTCCGTGGCACTTGTGCTTTCCTGGCTGAGAGCTCTCCCCTGTTGATAC | 497 |
| TPST2 | GGTGAACCAGAACAGCACCTCCTCCCACTTAGGAAGCTCGTGATTTCCAG | 498 |
| E4F1 | CTGGTAGAGAAGATGGCACAGGATGGAGGCGCCCCAAGACGGACAGTGTA | 499 |
| CST7 | TCACTGACCCCCGCCTCTTCAGCAAGACCACAGCCATGACAAACACCAGG | 500 |
| GNG4 | CTGTAAAAGTACCCCATACCGTTGACGCGCTGTGGCAGACCTGTGGGTGC | 501 |
| CD70 | GAGGGGACACACTCTGCACCAACCTCACTGGGACACTTTTGCCTTCCCGA | 502 |
| BACH2 | CCAGAGGCCATATTCAAAACAGGGTCTTCTCAGTGTATGCAAGGGGCTGC | 503 |
| REL | GGATCTGACTTCAGTTGTGCAGATAACAGCATGATAAATGAGTCGGGACC | 504 |
| PAM | GGCTACAGTCGAAAAGGGTTTGACCGGCTTAGCACTGAGGGCAGTGACCA | 505 |

TABLE VII-continued

Oligonucleotides/probes used for gene expression profiling.

| Gene name | Probe sequence | SEQ ID No: |
|---|---|---|
| KIAA0831 | GTGGACGGGACTCATGTAAGGACTCAATTTGGGGAAGAGCATTCAGTGGC | 506 |
| LOC197322 | CGCCAGAGGCCTGGACCCAAGGGAACGGCAGTCAGAGACTACAGTCCAGA | 507 |
| IL2RA | GGTTCCTTTCTCAGCCGCTTCTGACTGCTGATTCTCCCGTTCACGTTGCC | 508 |
| IL13 | GACCCACTTCACACACAGGCAACTGAGGCAGACAGCAGCTCAGGCACACT | 509 |
| LPIN1 | ACCCAGTGATGCTGAGGTCATGTGCTGGAATGCTGTATTTGGACCACACA | 510 |
| CBFA2T3 | TGCAATACGGGAGTGACCCAGCTACTGAACCAGCCACGAACAGCCCGCCA | 511 |
| KRT1 | GCAAGACCGAGGTCGATTTGTCCCAGCCTTACCGGAGAAAAGAGCTATGG | 512 |
| MT1A | TGCTGCTCCTGCTGCCCCATGAGCTGTGCCAAGTGTGCCCAGGGCTGCAT | 513 |
| ANKRD5 | GGTAGGCTATCAGGAAGTGCAGGCTGGAAACATGCAGGAGCTGTCCCTGA | 514 |
| NQO1 | GGCACTGGTGGTTTTGCTCTCGACAGTATCCACAATAGCTGACGGCTGG | 515 |
| KLF6 | TGCACCCTACCCAGTTGCCTCCAGGGCCTCTCCTTGGAAGGTCTTTTGAG | 516 |
| CENPE | CCAGAGGTGCAAAATGCAGGAGCAGAGAGTGTGGATTCTCAGCCAGGTCC | 517 |
| SMOX | CCCGTGCCCCCACTTGCCTACCCTCTGTCCTGCCTTGTTATTGTAAGTGC | 518 |
| FBXO34 | GAGCGCCTTTACCTTTAGATGAGTGCTTTGGCCCCTCTGTGAATAGCACG | 519 |
| LZTS1 | GGGCTGCTCACCCACCTCTTGTGCAAGGTGGCCTTTGTGCTGCGCCTGCA | 520 |
| LAMP3 | CTCTGCCTGAAGGCTCACACCTCATACCAGCATACGCTCACCTTACAGGG | 521 |
| SPEN | TGCCCACTCATTTGTATAAGTGCGCTTCGGTACAGCACGGGTCCTGCTCC | 522 |
| SH2B3 | AAGGCCTTGGACTCTTCCCTGAGGGTTGCCTGAAATTCCTTCATGCTTTC | 523 |
| TNF | CCGTGAAAACGGAGCTGAACAATAGGCTGTTCCCATGTAGCCCCCTGGCC | 524 |
| BAT2D1 | CAGAGCTGTGTCATGCCATCCTTTGGGCCCTCTGCTGGAAAAGTAGAATC | 525 |
| ZYX | TGGGAGACCCTCCAGGACATTCCCACCCTCCCCCATGCTGCCAAGTTGTA | 526 |
| SPTBN1 | CAGCGAGGTCCCTGTGAGTTTGAAAGAAGCTGTCTGCGAAGTGGCCCTTG | 527 |
| ATP1B1 | CTGACTTGTAGTAAGCAGTGTTTCTGGCCCCTAAGTATTGCTGCCTTGTG | 528 |
| SLA | GTGGTTTCCCCAACCGTTCCAAAAGGCTATTTCAAAGGAACCAGCCCACG | 529 |
| PLAU | GTGGTCTTTCTGGAGAGGTTATAGGTCACTCCTGGGGCCTCTTGGGTCCC | 530 |
| SOCS1 | CTCCTGGTGCTCCCTCTGGGTCCCCCTGGTTGTTGTAGCAGCTTAACTGT | 531 |
| OSGIN1 | CTGCGCCTTCCAGAAGCAGGTCCCAAATAAAGCCAGTGCCCACCTGAAAA | 532 |
| BRD2 | GCCCTGGGGTTTCAGTCATCTCCCCATTTGGTCCCCTGGACTGTCTTTG | 533 |
| VGF | TAATTGTGTGAAGTGTGTCTGTCTCCAGCCCTTCGGGCCTCCCACGAGCC | 534 |
| PTPN6 | GGAGAAGAGCAAGGGTTCCCTCAAGAGGAAGTGAGCGGTGCTGTCCTCAG | 535 |
| TNFSF14 | GGGTCTGACACGTGGAGAACTCAGAGGGTGCCTCAGGGGAAAGAAAACTC | 536 |
| IL2 | CCAGGATGCTCACATTTAAGTTTTACATGCCCAAGAAGGCCACAGAACTG | 537 |
| CD97 | GGGCGCTTGTCCCATCCTGGACTTTTCCTCTCATGTCTTTGCTGCAGAAC | 538 |
| RPL28 | CCCAAGCACCTGGAAGACATGCCAGATCCATGTGCAGTAATGCCTGGTGG | 539 |
| CSF2 | TGGACCTGCCCTGGGCCACACTGACCCTGATACAGGCATGGCAGAAGAAT | 540 |
| CCAR1 | GGCCTCATTGTGTACAATGGTGCAATGGTAGATGTAGGAAGCCTCTTGCA | 541 |
| RPL7L1 | GGGCTGAAAACTGCCCTTGGGCTGACTTTTGATAGGCCATGCCTTGCCAC | 542 |

TABLE VII-continued

Oligonucleotides/probes used for gene expression profiling.

| Gene name | Probe sequence | SEQ ID No: |
|---|---|---|
| CD83 | GCCTTCTGTAGGAATTCTTTTGGGGAAGTGAGGAAGCCAGGTCCACGGTC | 543 |
| MIDN | GAACCGGCTCGCCACCCTCTGCCCGGTAAGGGCTGCCCAAGAAAGCATTA | 544 |
| BCL2L1 | AGCGTGTCTGTATTTATGTGTGAGGAGCTGCTGGCTTGCAGTGCGCGTGC | 545 |
| LUZP1 | CAAGCATGGGACCAAGGAGGCCAGAACCTGTCGCTGGAAACCAGGGCAAA | 546 |
| VHL | TTCCTGTGCTCAAAAATGAGAGTGACGGCTGGCATGGTGGCTCCCGCCTG | 547 |
| CCL20 | CCTTGCTGGGGTTGGAGGTTTCACTTGCACATCATGGAGGGTTTAGTGCT | 548 |
| PCNT | GAGGTGACGGGCACTCACTCCCATGAGCCCTGGCTGTGTGCTGTTGTGTG | 549 |
| SPRY1 | GCCCTGGATAAGGAACAGCTACAGTCGCTGTTAAATGTGCCTGAAAAGCA | 550 |
| RUNX3 | AACCATCCCAGAGCTGGCGAGAGGATGGAGCTGGGTGGAAACTGCTTTGC | 551 |
| BCL2A1 | TGAATAACACAGGAGAATGGATAAGGCAAAACGGAGGCTGGGAAAATGGC | 552 |
| MBP | CTGCTCACTGTGTCCTTCTGTGGTCTCAGGAGCTGCAGTTGTTGCTGTTG | 553 |
| RHOU | GCAAGGCCTTCTCTCCAGACTATCGTAACCTGGTGCCTTACCAAGTTGTG | 554 |
| RDH10 | GTGCCCTTTCCTCAGGAAGTTGCTGTGTTTCATTTCTTTGGATGGACTCT | 555 |
| HTR2B | CCTGCCATGTACCAGAGTCCAATGAGGCTCCGAAGTTCAACCATTCAGTC | 556 |
| DDEF1 | GCATGAGGAACCAGTTGACATGCTGGGTTGTGACTGGCAGCTTTAGCAGC | 557 |
| GZMB | CGCCATTATTACGACAGTACCATTGAGTTGTGCGTGGGGGACCCAGAGAT | 558 |
| TJAP1 | GCCTGGCCCCACTCCCAACCTTGGCTCTAGACTGTTACTCTTAAGCTTT | 559 |
| MACF1 | GGGGCTGTCTGGGGCTCCTGTTTTTTAGCTGCTGTTCTTCAGCTCCGACC | 560 |
| RCBTB2 | GTCCTTACCACATTTTCAGCACTCAGCACAGTGCCTTGTGTATAATAGGC | 561 |
| RGS16 | GCCTGACTGTCTCCCTTTCTCTACCAGACTCTACCTCTGAATGTGCTGGG | 562 |
| JMJD1C | CACCAGCTATTGCCTGCATCTGGGAAATTGCTGAATCGCACAGCAGTCAT | 563 |
| SPRY1 | GCCTTCGTATTTGTGAAGGACTCAGCCACCTTCCTTCTTCACCCCATGCT | 564 |
| LTB | AGACCTTCTTTGGGGCCGTGATGGTGGGGTGAGGGAATATGAGTGCGTGG | 565 |
| MYH9 | CTAGGACTGGGCCCGAGGGTGGTTTACCTGCACCGTTGACTCAGTATAGT | 566 |
| CLIP3 | CAGCTCACGACTGCCCCTTCACTGCATGTCCCCAAACTCAGCATGACTCC | 567 |
| GBE1 | CTGCCGAATTGAAGAGGCCTGATTTCAGCTCCACCAGATGCAGATTTGTG | 568 |
| CCDC64 | CTCACGTGGGGAAAGCACAGCAGGGATGCGCGGCAAGAATGTACCTGTAG | 569 |
| PHEX | CATGGACTCCTGCCGACTCTGGTAGCTGGGACGCTGGTTTATGGCATCCT | 570 |
| SNX26 | GGGGGGACAACTCCTACCCTTCTTTCCCCACATGCCCCACTAAACCATCT | 571 |
| TAGAP | ATGAGAAATCCCCAACTTATGATCTCACCATCTGTTTGCCAAGTCCAGGC | 572 |
| FAM50A | CTTTTCCAATAAAGAAGTGCACGTGTCAGAGCTGGAGCGCCTGCATTGTG | 573 |
| TRAF1 | TCCCTACTCACCGAGTGTTGAGCCCAAGGGGGGATTTGTAGAACAAGCCC | 574 |
| CDK5RAP2 | AGTTGAGGCTGTGCGCCTTGGTGGGCTTCACGTCTTCCCCTGGATTTGCT | 575 |
| TAF1C | GACTCACACAAACAGGAGCTAGCCCAATCATACACTGACTCGCGTGGGTG | 576 |
| KIAA1754 | GCCTCCAGAAGCCAAAACCATGCCTGGATCTCCCATAGCTTCTCCTTTGC | 577 |
| LRRC8C | TGAAATCCTCCCTCCTGAACTGGGTGACTGTCGGGCTCTGAAGCGAGCTG | 578 |
| SUPT6H | CAAGCCATTTTGAACTTCTGCCCTCACCGGACTCTGGGCTGTGACTGGGG | 579 |
| IL23A | GAGTCCCTAAAGGCAGCAGCTCAAGGATGGCACTCAGATCTCCATGGCCC | 580 |

TABLE VII-continued

Oligonucleotides/probes used for gene expression profiling.

| Gene name | Probe sequence | SEQ ID No: |
|---|---|---|
| SH2D2A | GCAAAGAAGTGTGCAAGGAGGGCCCTGTTAGCTCCCACTGTCCTGGTTTC | 581 |
| IL21R | GCTGGGCCCCTACCCTGCCCCAATTCAATCCTGCCAATAAATCCTGTCT | 582 |
| ATP6V0A4 | GGACGTCAGCCTGTGGATTTGATACGACTTAACCACGTCAGAGGAAGGAC | 583 |
| TNFRSF8 | CCGCTCAGATGTTTTGGGGAAAGTTGGAGAAGCCGTGGCCTTGCGAGAGG | 584 |
| MAPRE2 | CCCTCTTTAACACAAGGGCCCTCCTTGTCATTGACCTTAGCTAAACCATG | 585 |
| TMEM158 | GAACCTTTTCCAAGTTGATCTATCCAGTGACGTGGCCTGGTGGGCGTTTC | 586 |
| ITGA5 | GCCCAACCCTTCCCTCACCTTGGCACCAGACACCCAGGACTTATTTAAAC | 587 |
| JAM3 | GAATGTGACTCAAGACTCGAGGCCGATACGAGGCTGTGATTCTGCCTTTG | 588 |
| BAZ1A | CTGCACTGTCTGCAGTTGCATCTTTGGCAGCTGCATGGCCACAGTTACAC | 589 |
| IL3 | GAGCCTCGCGATCTTTTGAGTCCAACGTCCAGCTCGTTCTCTGGGCCTTC | 590 |
| FOS | CCCAGTGACACTTCAGAGAGCTGGTAGTTAGTAGCATGTTGAGCCAGGCC | 591 |
| HES4 | CCCCGTTCTAGGGCCGTGGCCTTTGCCGAGACTGTAGCAGAGAAAACGTA | 592 |
| TIMP1 | AGTCCCTGCGGTCCCAGATAGCCTGAATCCTGCCCGGAGTGGAAGCTGAA | 593 |
| TNS3 | GCGGAGAGTTCACGAACTGTGCCCAACGCATGTTATAGCCAGGGTCCTAC | 594 |
| NFKBIA | GAGGACGAGCTGCCCTATGATGACTGTGTGTTTGGAGGCCAGCGTCTGAC | 595 |
| CGA | ACAGGGTCACAGTAATGGGGGGTTTCAAAGTGGAGAACCACACGGCGTGC | 596 |
| TSC22D1 | GGTGACAGGTAGCTGGGACCTAGGCTATCTTACCATGAAGGTTGTTTTGC | 597 |
| ATP1B1 | GCTGTGTCTGAGATCTGGATCTGCCCATCACTTTGGCTAGTGACAGGGCT | 598 |
| EIF4G3 | TGGGAAGGGCGTGGCTCTGAAATCTGTCACGGCATTCTTCACGTGGCTGC | 599 |
| ATP6V1B2 | TCCTGCGCCTTCCTGACGTGAGCCCTGAGCGATCTTCTATGCAGTTCTGC | 600 |
| DUSP1 | GCAGAAGAGAAAGGACTCAGTGTGTGATCCGGTTTCTTTTTGCTCGCCCC | 601 |
| SLC9A1 | TCCTCGGCCCATCTGTCCATCCTCCTCTCCATGCAAGTGCTGTTTGGGCA | 602 |
| MEF2D | TCTTCCTGGGTCCTGGGGCAGGGCGAGTCCAAGTGTGAGGCTGTTGATTT | 603 |
| SNAPC4 | GGCCTGCCGACTGACTGTGTGGCATGGAGCATGGCTGTTCCCCAAGTGCA | 604 |
| GPR171 | GCCAAAGAGGCTACACTGCTCCTGGCTGTGTCGAACCTGTGCTTTGATCC | 605 |
| CD27 | GGCAGGGACGAGGACAAATATGGATGAGGTGGAGAGTGGGAAGCAGGAGC | 606 |
| ALDOC | CCATGATGAGGTAGCTTCTCCCTGGGCTCTCCTTCTTGCCTGCCCTGTCT | 607 |
| TNFRSF21 | AAAGGTGGCGTGGACTCCCTTTGTGTGGGTGGGGTTTGTGGGTAGTGGTG | 608 |
| DPP9 | TGAAACGCACCGAACTTCCACGCTCTGCTGGTCAGTGGCGGCTGTCCCCT | 609 |
| SRRM2 | GAGGCATGGCCCCACTTGTATCCAGAAGTTCCCAGGGGTGATTGTGATGG | 610 |
| METT11D1 | CCCGTATCACTCAGCCTGTCCTTAAACGGCCTCGCCATGTGCATTGTCAC | 611 |
| CD69 | AGGCGTGGACTTACTATTTATTGCTGAATGACTACCAACAGTGAGAGCCC | 612 |
| IRX5 | GAAAGGTATGTCCGACATTTAACGCGGGCTGCGTCGGTCCCGGACTTTTC | 613 |
| TBC1D10C | CCGTGGTACATACTGGGTCAGGCACTAGCATGGAGGAGGGTCACAGAGTG | 614 |
| KLF6 | CCCTTCCGAGCGGCGCCTAAGCCTTTGCCGTGAGCATGCACACTGAGAAT | 615 |
| PLAGL2 | CCACTTGCACCTCTCCACCTTTGGCACTAGAACTCCTGAGACACCACTTC | 616 |
| KLF2 | ATTACTGTACATAGAGAGACAGGTGGGCATTTTTGGGCTACCTGGTTCGT | 617 |

TABLE VII-continued

Oligonucleotides/probes used for gene expression profiling.

| Gene name | Probe sequence | SEQ ID No: |
|---|---|---|
| PRR14 | GCCCCATCTGTTGGTCATCCATCCTGAAGGGACAGGAAACCTCCCAGGCA | 618 |
| BIRC3 | GAAACATTCTAGTAGCCTGGAGAAGTTGACCTACCTGTGGAGATGCCTGC | 619 |
| FSCN1 | CAGCCTCCCCCGTCCCCAACATGCATCTCACTCTGGGTGTCTTGGTCTTT | 620 |
| IGFBP2 | CAAACACCGGCAGAAAACGGAGAGTGCTTGGGTGGTGGGTGCTGGAGGAT | 621 |
| LTBP4 | TGGACCTGGAGAAGGGACCTACGGACGCCTGGAAGCTGCGACGCCCTGCA | 622 |
| USP11 | GCCCCGCCTGTGTTTGCCCTTCCAGCAGTGACCCTCCCTTCTAGTCTTTA | 623 |
| BHLHB2 | GGTCCAGAGTACTTGTTTTCCCGATGTGTCCAGCCAGCTCCGCAGCAGCT | 624 |
| ARC | CAGACCACTCTGACAAGTCTTCAGCCCACACCCTGCCAGCCCCACAGATT | 625 |
| PPP1R15A | CCCTGGACCTCAGTGGGAGGCGTGGCTGAGACCAACTGGTTTGCCTATAA | 626 |
| AUTS2 | GTGAAGCAACTGAATCTTCAGCATGTTCTCATCGGCGGAGCCTTCTTGTG | 627 |
| RXRA | AAGCCTTGCTCTGTTGTGTCCTGTTGCCGGCTCTGGCCTTCCTGTGACTG | 628 |
| MARVELD3 | GATGCAACAGACCCTGGCTTCTGGAGTCCTCTGTGAGTGAGGGACCAATC | 629 |
| ARG2 | CATTTTGGGGTTAGACCTGGGACCACGGCTGGATACTCTGAGGCTGTATG | 630 |
| SETD2 | GACCTGACTCCACTCTTAAACCTGGGTCTTCTCCTTGGCGGTGCTGTCAG | 631 |
| CENPF | CCAGTGAGGGCTGCAGGCTTCCTAGAGGTGTGCTATACCATGCGTCTGTC | 632 |
| ADORA2A | GCTGGGATCAAGGATAGGGAGTTGTAACAGAGCAGTGCCAGAGCATGGGC | 633 |
| FOSB | TGACTGTCCCTGCCAATGCTCCAGCTGTCGTCTGACTCTGGGTTCGTTGG | 634 |
| EGR2 | GCATGCAATTGTGTTGGAAGTGTCCTTGGTCGCCTTGTGTGATGTAGACA | 635 |
| LAIR2 | CTGAAGCCTCCGGATTTGATGCACCATGAATGAGGAGAAATGGCCTCCCG | 636 |
| CBX6 | GTGAGTGACCACCTGGGTGCCAGTTACAGGTGTTTCCAGAGACCATAGAA | 637 |
| PHACTR4 | CCTGAGCTACTTGTTCGCCTTCTGTGCGTCACCAAGTAATCTGGTTCATC | 638 |
| CCL4L1 | AACTTTGTGGTAGATTACTATGAGACCAGCAGCCTCTGCTCCCAGCCAGC | 639 |
| ULK1 | GCGCCTCAACTGCTGCCCCTGGTTGAATGTTCTCTTGATAGTGCTGGACC | 640 |
| PTPN22 | TTGTGGGTTGCAATACAAACTGCTCTTGACAATGACTATTCCCTGACAGT | 641 |
| GNL3L | CCAAGCCCTGGAGACCCATTACCACCGTTAACCCTCAATACAGCTCTGCT | 642 |
| ZCCHC6 | AATTTCAAAAGCCCTGCAGACATAGTACCTGGTCAGAACTATGCCTCGGT | 643 |
| PRKCH | AGAAGGGTCACTGCCACAACAGCACAGTCAGCGGGTGAATTACAGGTGCC | 644 |
| MFSD2 | AGCTGGACTGCAGGTGCTAGGAAGGGAACTGAAGACTCAAGGAGGTGGCC | 645 |
| BIRC3 | GGCATTGTACTAATACCGGGAACATGAAGCCAGGTGTGGTGGTATGTGCC | 646 |
| TMEM187 | GGCAAGGGGAGTGGAAATGACACCAAGAAGCCCCTCATGCTCATGGTTGG | 647 |
| C6orf190 | GGCCACAGCGAATCTTAACCTAACAGCCTTGACAAACTGCACCATAGGTG | 648 |
| ITPR3 | AGGGCTGAGCTGCGCTTGCGTGGCTGTTTCATGACCGCTTGTTTTTCTCC | 649 |
| ADM | GTCTCAGCGAGGTGTAAAGTTGTTCGCCGCGTGGAATGTGAGTGTGTTTG | 650 |
| MT2A | TGCGCCTGATGCTGGGACAGCCCCGCTCCCAGATGTAAAGAACGCGACTT | 651 |
| EOMES | GTCCAGGATTGCCTCACTTGAGACTTGCTAGGCCTCTGCTGTGTGCTGGG | 652 |
| POU2AF1 | ATAAGCCACCATTCTGTGGAACCAAGGCCCCCTCCACGCAAACACCCTCC | 653 |
| NFATC1 | CAGCCAAGGGGAAAACATGGCTCTTCTGCTCCAAAAAACTGAGGGGTCC | 654 |
| C1orf165 | CCGAGCCGGAGTTACGGAGCACTTTCAGTGAGGAAGCAAATACGTCGTCC | 655 |

TABLE VII-continued

Oligonucleotides/probes used for gene expression profiling.

| Gene name | Probe sequence | SEQ ID No: |
|---|---|---|
| ZFP36 | CCAGTGTCTCCTGGTAACTGGAACCTCTCCTGAGGGGGAATCCTGGTGCT | 656 |
| BCL9 | CCTTTCCTCCCCCTCCCATGCGTAAGACGTTCTGTGTAACCTCCATTAAA | 657 |
| NOTCH1 | GTGGTGCCATCCCCAGGGGGCATGACCAGATGCGTCCCAAGATGTTGATT | 658 |
| POLE | GAGCCAGCCTTAGTTTGTCCCTGCCATCTACTGTCTGAGGCCATCGCTGC | 659 |
| LY96 | TGGGAGCCCAGAAGAAATGCTCTTTTGCTTGGAGTTTGTCATCCTACACC | 660 |
| CREBBP | GGGCGTCTCCCAGTATTACCCTGGATGATAGGAATTGACTCCGGCGTGCA | 661 |
| EGR4 | TTTGTAACTGCACACGCCCCACGCCTTCCTCTATAACCCCCAGAGACAGG | 662 |
| ACVR1 | TTCAGTTCATATGCAGAACGTATTTAGCCATTACCCACGTGACACCACCG | 663 |
| PFKFB4 | GCTGGCGTGCCCATGTTGCAGATATTTTCCCGAGTTCCCCAGAATGGATG | 664 |
| NR4A2 | GTTGCGTGGGTGGCATGAGTTGAAGAAGGCAAAGGCTTGTAAATTTACCC | 665 |
| MYC | CATCCTGTCCGTCCAAGCAGAGGAGCAAAAGCTCATTTCTGAAGAGGACT | 666 |
| CCL1 | CAAGCTGAAGAGAGGCAAAGAGGCCTGCGCCTTGGACACAGTTGGATGGG | 667 |
| CXCR3 | ACTTCATCTTCCCCAAGTGCGGGGAGTACAAGGCATGGCGTAGAGGGTGC | 668 |
| ICOS | GTCCAAGCTGTGCCTCGACACATCCTCATCCCAGCATGGGACACCTCAA | 669 |
| MAG1 | TCCTTGTTTGAATGCTGTAGATCTGTACCTAGTACCCCTCCCATCTACTG | 670 |
| FXYD5 | GTCGGTCTCACTGACATCATGGCTGACCCCAGCATCGCCTGGTCCCACAG | 671 |

Although the present invention has been described hereinabove by way of specific embodiments thereof, it can be modified, without departing from the spirit and nature of the subject invention as defined in the appended claims.

The present description refers to a number of documents, the content of which is herein incorporated by reference in their entirety.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08647822B2). An electronic copy of the "Sequence Listing" will also be available from the USPTO upon request and payment of the fee set forth in 37 CFR 1.19(b)(3).

What is claimed is:

1. A method of determining whether a test compound modulates PD-1 activity comprising:
   (a) providing an activated immune cell expressing PD-1;
   (b) determining a gene expression profile of said immune cell in the presence of said test compound;
   (c) comparing said gene expression profile to a corresponding reference gene expression profile determined in the absence of said test compound;
      wherein said gene expression profile comprises a candidate expression value for at least two genes, wherein said at least two genes are selected from CD55, NFKB2, FAM65A, DIP, STS-1, TPST2, E4F1, CST7, GNG4, CD70, BACH2, REL, PAM, KIAA0831, LOC197322, IL2RA, IL13, LPIN1, CBFA2T3, KRT1, MT1A, ANKRD5, NQO1, KLF6, CENPE, SMOX, FBXO34, LZTS1, LAMP3, SPEN, SH2B3, TNF, BAT2D1, ZYX, SPTBN1, ATP1B1, SLA, PLAU, SOCS1, OSGIN1, BRD2, VGF, PTPN6, TNFSF14, IL2, CD97, RPL28, CSF2, CCAR1, RPL7L1, CD83, MIDN, BCL2L1, LUZP1, VHL, CCL20, PCNT, SPRY1, RUNX3, BCL2A1, MBP, RHOU, RDH10, HTR2B, DDEF1, GZMB, TJAP1, MACF1, RCBTB2, RGS16, JMJD1C, SPRY1, LTB, MYH9, CLIP3, GBE1, CCDC64, PHEX, SNX26, TAGAP, FAM50A, TRAF1, CDK5RAP2, TAF1C, KIAA1754, LRRC8C, SUPT6H, IL23A, SH2D2A, IL21R, ATP6V0A4, TNFRSF8, MAPRE2, TMEM158, ITGA5, JAM3, BAZ1A, IL3, FOS, HES4, TIMP1, TNS3, NFKBIA, CGA, TSC22D1, ATP1B1, EIF4G3, ATP6V1B2, DUSP1, SLC9A1, MEF2D, SNAPC4, GPR171, CD27, ALDOC, TNFRSF21, DPP9, SRRM2, METT11D1, CD69, IRX5, TBC1D10C, KLF6, PLAGL2, KLF2, PRR14, BIRC3, FSCN1, IGFBP2, LTBP4, USP11, BHLHB2, ARC, PPP1R15A, AUTS2, RXRA, MARVELD3, ARG2, SETD2, CENPF, ADORA2A, FOSB, EGR2, LAIR2, CBX6, PHACTR4, CCL4L1, ULK1, PTPN22, GNL3L, ZCCHC6, PRKCH, MFSD2, BIRC3, TMEM187, C6orf190, ITPR3, ADM, MT2A, EOMES, POU2AF1, NFATC1, C1orf165, ZFP36, BCL9, NOTCH1, POLE, LY96, CREBBP, EGR4, ACVR1, PFKFB4, NR4A2, MYC, CCL1, CXCR3, ICOS, MAG1 and FXYD5;

wherein said gene expression profile determined after about 30 minutes of activation, comprises a candidate expression value for at least two genes selected from FAM65A, E4F1, CBFA2T3, CENPE, SPEN, TNF, BAT2D1, SPTBN1, BRD2, CCAR1, RPL7L1, MIDN, VHL, PCNT, RUNX3, TJAP1, MACF1, MYH9, CLIP3, SNX26, CDK5RAP2, BAZ1A, FOS, EIF4G3, DUSP1, SLC9A1, MEF2D, SNAPC4, SRRM2, PHACTR4, ULK1, GNL3L, ZCCHC6, ITPR3, ZFP36, NOTCH1, POLE and EGR4;

wherein said gene expression profile determined after about 3 hours of activation, comprises a candidate expression value for at least two genes selected from E4F1, CBFA2T3, MT1A, ANKRD5, KLF6, SPEN, TNF, BAT2D1, ZYX, SPTBN1, SLA, SOCS1, OSGIN1, BRD2, VGF, TNFSF14, RPL28, CSF2, CCAR1, RPL7L1, MIDN, LUZP1, VHL, PCNT, SPRY1, RUNX3, RDH10, DDEF1, GZMB, TJAP1, MACF1, JMJD1C, SPRY1, MYH9, CLIP3, SNX26, TAGAP, FAM50A, CDK5RAP2, TAF1C, KIAA1754, SUPT6H, SH2D2A, ATP6V0A4, TNFRSF8, ITGA5, IL3, TIMP1, SLC9A1, MEF2D, SNAPC4, DPP9, SRRM2, CD69, IRX5, KLF6, PLAGL2, KLF2, PRR14, FSCN1, LTBP4, USP11, BHLHB2, ARC, PPP1R15A, AUTS2, MARVELD3, SETD2, CENPF, CBX6, ULK1, GNL3L, ZCCHC6, ITPR3, MT2A, NFATC1, ZFP36, BCL9, NOTCH1, POLE, CREBBP, ACVR1, ICOS and MAG1;

wherein said gene expression profile determined after about 6 hours of activation, comprises a candidate expression value for at least two genes selected from CD55, DIP, STS-1, CD70, BACH2, REL, KIAA0831, CBFA2T3, KLF6, SMOX, FBXO34, LZTS1, LAMP3, SPEN, SH2B3, ATP1B1, SLA, PLAU, SOCS1, BRD2, PTPN6, TNFSF14, CD97, CSF2, CD83, SPRY1, RUNX3, MBP, RDH10, SPRY1, LTB, MYH9, CCDC64, TAGAP, TRAF1, LRRC8C, IL23A, SH2D2A, IL21R, MAPRE2, TMEM158, IL3, FOS, TNS3, NFKBIA, TSC22D1, ATP1B1, ATP6V1B2, DUSP1, SLC9A1, GPR171, CD27, TNFRSF21, TBC1D10C, KLF6, LTBP4, MARVELD3, ADORA2A, CCL4L1, PTPN22, PRKCH, BIRC3, C6orf190, ADM, EOMES, POU2AF1, NFATC1, LY96, ACVR1, MYC, CCL1, CXCR3, MAG1 and FXYD5;

wherein said gene expression profile determined after about 18 hours of activation, comprises a candidate expression value for at least two genes selected from CD55, NFKB2, TPST2, CST7, GNG4, CD70, REL, PAM, KIAA0831, LOC197322, IL2RA, IL13, CBFA2T3, KRT1, MT1A, NQO1, FBXO34, LAMP3, TNFSF14, IL2, CD97, CSF2, CD83, BCL2L1, CCL20, SPRY1, BCL2A1, MBP, RHOU, RDH10, HTR2B, GZMB, RCBTB2, RGS16, SPRY1, LTB, GBE1, CCDC64, PHEX, TAGAP, TRAF1, CDK5RAP2, LRRC8C, IL23A, SH2D2A, IL21R, ATP6V0A4, ITGA5, JAM3, IL3, HES4, TNS3, NFKBIA, CGA, ATP6V1B2, GPR171, CD27, ALDOC, METT11D1, CD69, PLAGL2, KLF2, BIRC3, IGFBP2, RXRA, ARG2, CENPF, ADORA2A, LAIR2, PTPN22, GNL3L, MFSD2, BIRC3, TMEM187, C6orf190, ADM, POU2AF1, C1orf165, PFKFB4, NR4A2, CCL1 and ICOS and wherein said reference gene expression profile comprises a reference expression value for said at least two genes; and (d) determining whether said test compound modulates PD-1 activity based on said comparison.

2. The method of claim 1, wherein (i) said reference expression value corresponds to the level of expression of said at least two genes in the absence of an inhibitor or agonist of PD-1 activity and wherein a difference in said gene expression profile relative to said reference gene expression profile is indicative that said test compound modulates PD-1 activity;

(ii) said reference expression value corresponds to the level of expression of said at least two genes in the presence of an inhibitor of PD-1 activity, and wherein a similarity in said gene expression profile relative to said reference gene expression profile is indicative that said test compound inhibits PD-1 activity; or (iii) said reference expression value corresponds to the level of expression of said at least two genes in the presence of an agonist of PD-1 activity, and wherein a similarity in said gene expression profile relative to said reference gene expression profile is indicative that said compound increases PD-1 activity.

3. The method of claim 1, wherein said expression value is obtained by determining the level of expression of a nucleic acid or polypeptide encoded thereby comprising a sequence selected from SEQ ID NOs: 1-492.

4. The method claim 1, wherein said immune cell is a T cell.

5. The method of claim 4, wherein said T cell is a $CD4^+$ T cell.

6. The method of claim 1, further comprising activation of a T cell thereby to provide said activated T cell.

* * * * *